US 12,252,506 B2

(12) United States Patent
Migaud et al.

(10) Patent No.: US 12,252,506 B2
(45) Date of Patent: *Mar. 18, 2025

(54) METHODS OF PREPARING NICOTINAMIDE RIBOSIDE AND DERIVATIVES THEREOF

(71) Applicant: The Queen's University of Belfast, Belfast (GB)

(72) Inventors: Marie Migaud, Lurgan (GB); Philip Redpath, Portadown (GB); Kerri Crossey, Magherafelt (GB); Mark Doherty, Newtownabbey (GB)

(73) Assignee: The Queen's University of Belfast, Belfast (GB)

( * ) Notice: Subject to any disclaimer, the term of this patent is extended or adjusted under 35 U.S.C. 154(b) by 6 days.

This patent is subject to a terminal disclaimer.

(21) Appl. No.: 18/307,733

(22) Filed: Apr. 26, 2023

(65) Prior Publication Data
US 2024/0101588 A1 Mar. 28, 2024

Related U.S. Application Data

(63) Continuation of application No. 17/736,834, filed on May 4, 2022, now Pat. No. 11,981,698, which is a continuation of application No. 16/886,985, filed on May 29, 2020, now Pat. No. 11,584,770, which is a continuation of application No. 15/905,922, filed on Feb. 27, 2018, now Pat. No. 10,815,262, which is a continuation of application No. 14/908,831, filed as application No. PCT/EP2014/065971 on Jul. 24, 2014, now Pat. No. 10,000,519.

(30) Foreign Application Priority Data

Jul. 29, 2013 (GB) ..................... 1313465

(51) Int. Cl.
*C07H 19/048* (2006.01)
*C07H 1/00* (2006.01)
*C07H 1/06* (2006.01)
*C07H 19/04* (2006.01)

(52) U.S. Cl.
CPC ............ *C07H 19/048* (2013.01); *C07H 1/00* (2013.01); *C07H 1/06* (2013.01); *C07H 19/04* (2013.01); *Y02P 20/582* (2015.11)

(58) Field of Classification Search
None
See application file for complete search history.

(56) References Cited

U.S. PATENT DOCUMENTS

| | | |
|---|---|---|
| 6,689,760 B1 | 2/2004 | Yatvin et al. |
| 10,000,519 B2 | 6/2018 | Migaud et al. |
| 11,584,770 B2 | 2/2023 | Migaud et al. |
| 2018/0186824 A1 | 7/2018 | Migaud et al. |

FOREIGN PATENT DOCUMENTS

| | | |
|---|---|---|
| WO | WO 1993/08288 | 4/1993 |
| WO | WO 2002/04478 | 1/2002 |
| WO | WO 2007/061798 | 5/2007 |
| WO | WO 2011/081942 | 7/2011 |

OTHER PUBLICATIONS

U.S. Appl. No. 14/908,831, filed Jan. 29, 2016, Patented.
U.S. Appl. No. 15/905,922, filed Feb. 17, 2018, Patented.
U.S. Appl. No. 16/886,985, filed May 29, 2020, Patented.
U.S. Appl. No. 17/736,834, filed May 5, 2022, Pending.

(Continued)

*Primary Examiner* — Patrick T Lewis
(74) *Attorney, Agent, or Firm* — Leydig, Voit & Mayer, Ltd.

(57) ABSTRACT

Methods of preparing nicotinamide riboside and derivatives thereof. In an aspect, the invention relates to a method of preparing a compound of formula (I)

(I)

Figure 1:
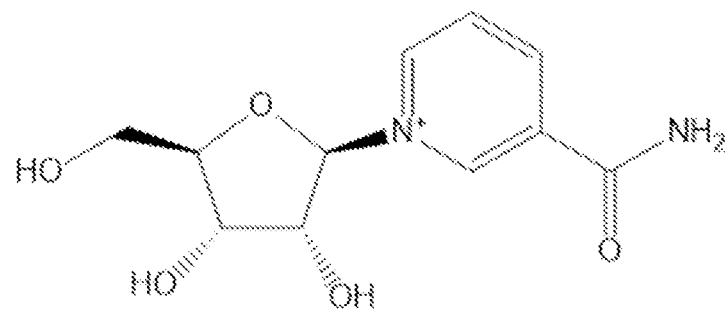
Figure 1:
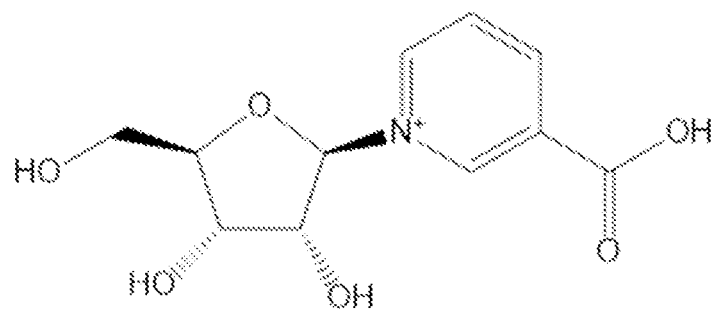
Figure 1:
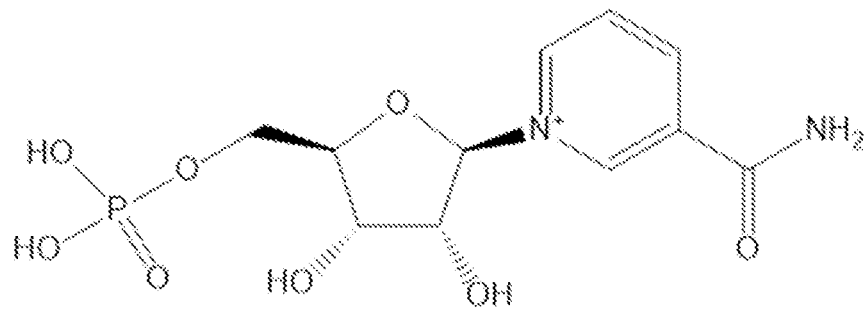
Figure 1:
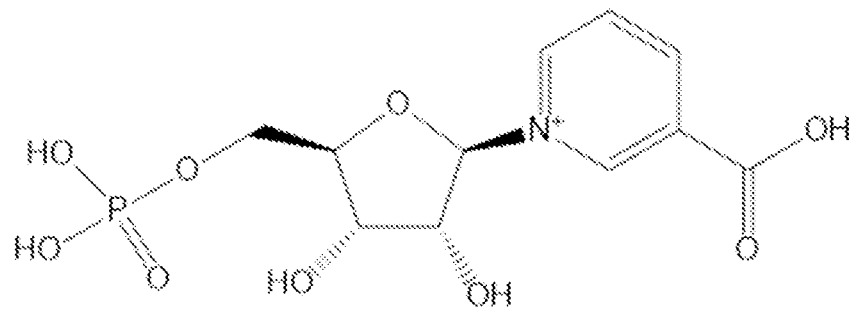

wherein
n is 0 or 1;
m is 0 or 1;
Y is O or S;
$R_1$ is selected from H, substituted or unsubstituted alkyl, substituted or unsubstituted alkenyl, substituted or unsubstituted alkynyl, substituted or unsubstituted aryl, substituted or unsubstituted primary or secondary amino, and substituted or unsubstituted azido;
$R_2$-$R_5$, which may be the same or different, are each independently selected from H, substituted or unsubstituted alkyl, substituted or unsubstituted alkenyl, substituted or unsubstituted alkynyl, and substituted or unsubstituted aryl; and
$X^-$ is an anion, selected from an anion of a substituted or unsubstituted carboxylic acid, a halide, a substituted or unsubstituted sulfonate, a substituted or unsubstituted phosphate, a substituted or unsubstituted sulfate, a substituted or unsubstituted carbonate, and a substituted or unsubstituted carbamate.

43 Claims, 5 Drawing Sheets

(56) References Cited

OTHER PUBLICATIONS

Bogan, Katrina L., et al. "Identification of Isn1 and Sdt1 as glucose-and vitamin-regulated nicotinamide mononucleotide and nicotinic acid mononucleotide 5'-nucleotidases responsible for production of nicotinamide riboside and nicotinic acid riboside." Journal of Biological Chemistry 284.50 (2009): 34861-34869.

D. Orain et al., "Protecting Groups in Solid-Phase Organic Synthesis," Journal of Combinatorial Chemistry 4(1): 1-16, 2002.

E. J. Freyne et al., "Stereospecific synthesis of a novel series of pyridine nucleosides," Carbohydrate Research 78(2):235-242, Jan. 15, 1980.

Extended European Search Report, EP Application No. 17191481.5, issued Mar. 1, 2018, 17 pages.

Franchetti et al., Stereoselective synthesis of nicotinamide ß-riboside and nucleoside analogs, Bioorganic & Medicinal Chemistry Letters 14:4655-4658, 2004.

H. G. Howell et al., (1988) "Antiviral Nucleosides. A Stereospecific, Total Synthesis of 2'-Fluoro-2'-deoxy-B-D-arabinofuranosyl Nucleosides," J. Org. Chem. 53(1): 85-88.

I. A. Mikhailopulo et al., "Synthesis of glycosides of nicotinamide and nicotinamide mononucleotide," Synthesis 1981(5):388-389, Jan. 1, 1981.

J. Lee et al., "A chemical synthesis of nicotinamide adenine dinucleotide (NAD+)," Chemical Communications 8, Jan. 1, 1999, pp. 729-730.

Jarman, M. "4-Substituted nicotinic acids and nicotinamides. Part III. Preparation of 4-methylnicotinic acid riboside." Journal of the Chemical Society C: Organic 6 (1969): 918-920.

L. F. Tietze et al., "Synthese von 1,4-dihydropyridinnucleosiden durch photochemische cycloaddition," Angew. Chemie 97(2):135-136, Feb. 1, 1985, with English Abstract.

L. J. Haynes et al., "Codehydrogenases, Part II. A synthesis of nicotinamide nucleotide," Journal Chemical Society, pp. 3727-3732, Jan. 1, 1957.

M. Jarman et al., "4-Substituted nicotinic acids and nicotinamides. Part II. The preparation of 4-methylnicotinamide riboside," J. Chem. Soc. (C): 199-203, 1969.

M. L. Sinnott et al., "Preparation and conformation of [alpha]-1-arabinofuranosyl-pyridinium salts, and hydrolysis of the 4-bromoisoquinolinium compound," Carbohydrate Research 136:357-368, Feb. 1, 1985.

M. R. Atkinson et al., "98. Synthesis of glycosylpyridinium compounds from glycosylamines and from glycosyl halides," Journal of the Chemical Society, pp. 610-615, Jan. 1, 1965.

M. Takatani et al., "Pentafluoropropionyl and trifluoroacetyl groups for temporary hydroxyl group protection in oligomannoside synthesis," Carbohydrate Research 338: 1073-1081, 2003.

N. J. Oppenheimer, "Synthesis of nicotinamide furanosides. Proton NMR study of the solution conformation of .alpha. and .beta., oxidized and reduced nicotinamide xylosides," Journal of Carbohydrates, Nucleosides, Nucleotides 5(3):251-260, Jan. 1, 1978.

N. L. Lifshits et al., "Synthesis and properties of nicotinic acid derivatives containing 2,2,6,6-tetramethylpiperidin-1-oxyl residue," Chemical Abstracts Database, Database accession No. 85-177804, Jan. 1, 1976.

Nikiforov et al. The Journal of Biological Chemistry (2011), vol. 286, pp. 21767-21778.

R. J. Knox et al., "Virtual cofactors for an *Escherichia coli* nitroreductase enzyme: Relevance to reductively activated prodrugs in antibody directed enzyme prodrug therapy (adept)," Biochemical Pharmacology 49(11):1647-1647, Jan. 1, 1995.

R. Riemschneider et al., "The effects of nonphysiological compounds on metabolism, IV. Nicotinylamino acid esters and nucleoside derivatives," pp. 99-106, Jan. 1, 1976.

S. Ladame et al., "Selective inhibition of trypanosoma cruzi GAPDH by "bi-substrate" analogues," Organic & Biomolecular Chemistry 3(11):2070-2072, Jan. 1, 2005.

Tanimori et al., "An efficient chemical synthesis of nicotinamide riboside (NAR) and analogues", Bioorganic & Medicinal Chemistry Letters 12(8):1135-1137, 2002.

Yang et al., "Syntheses of nicotinamide riboside and derivatives: Effective agents for increasing nicotinamide adenine dinucleotide concentrations in mammalian cells," Journal of Medicinal Chemistry 50:6458-6461, 2007.

International Preliminary Report on Patentability corresponding to International Application No. PCT/EP2014/065971, issued Feb. 2, 2016.

International Search Report and Written Opinion corresponding to International Application No. PCT/EP2014/065971, mailed Sep. 4, 2014, 10 pages.

Nicotinamide riboside

Nicotinate riboside

Nicotinamide mononucleotide

Nicotinate mononucleotide triacetyl-1,4-dihydronicotinamide riboside triacetyl O-ethyl-1,4-dihydronicotinate riboside tribenzoyl-1,4-dihydronicotinamide riboside reduced nicotinamide riboside
(1-(beta-D-ribofuranosyl)-1,4-dihydronicotinamide)

nicotinamide riboside, chloride salt nicotinamide riboside, acetate salt nicotinamide riboside, formate salt nicotinamide riboside, trifluoroacetate salt

METHODS OF PREPARING NICOTINAMIDE RIBOSIDE AND DERIVATIVES THEREOF

CROSS-REFERENCE TO RELATED APPLICATIONS

This application is a continuation of U.S. application Ser. No. 17/736,834, filed May 5, 2022, which is a continuation of U.S. application Ser. No. 16/886,985, filed May 29, 2020, now U.S. Pat. No. 11,584,770, which is a continuation of U.S. application Ser. No. 15/905,922, filed Feb. 27, 2018, now U.S. Pat. No. 10,815,262, which is a continuation of U.S. application Ser. No. 14/908,831, filed Jan. 29, 2016, now U.S. Pat. No. 10,000,519, which is a U.S. National Stage under 35 U.S.C. 371 of PCT/EP2014/065971, filed Jul. 24, 2014, and which claims priority from United Kingdom Patent Application No. 1313465.5, filed on Jul. 29, 2013. Each of these applications is incorporated by reference herein in its entirety.

FIELD OF THE INVENTION

The invention relates to methods of preparing nicotinamide riboside and derivatives thereof.

BACKGROUND TO THE INVENTION

Nicotinamide riboside and derivatives thereof, including nicotinate riboside, nicotinamide mononucleotide and nicotinate mononucleotide, are metabolites of nicotinamide adenine dinucleotide ($NAD^+$). The β-anomer forms of nicotinamide riboside, nicotinate riboside, nicotinamide mononucleotide and nicotinate mononucleotide are shown, without counter ions, in FIG. 1. As a $NAD^+$ precursor, nicotinamide riboside has been shown in mice to enhance oxidative metabolism and protect against high-fat diet induced obesity, which has resulted in significant interest in nicotinamide riboside and its derivatives. Since nicotinamide riboside is a naturally occurring compound, nicotinamide riboside and its derivatives have great potential as natural, nutritional supplements, which may provide health benefits without causing side effects. One limitation in the commercial exploitation of nicotinamide riboside and derivatives thereof, as nutritional supplements, or otherwise, is that known synthetic protocols for preparing nicotinamide riboside and derivatives thereof have disadvantages, rendering them unsuitable for scaling up for commercial or industrial use.

WO 2007/061798 describes a method for the preparation of nicotinamide riboside and derivatives thereof. However, the disclosed method has a number of disadvantages. For example, trimethylsilyl trifluoromethanesulfonate (TMSOTf) is used as the catalyst in the disclosed method, and results in the prepared compounds inevitably being in the form of their triflate ($^-$OTf) salts. The triflate salt form of nicotinamide riboside, or derivatives thereof, is not suitable for use as a nutritional supplement, because of its associated toxicity. Thus, the compounds produced by the disclosed method are not suitable for use as they are prepared, and require an additional step to exchange the triflate anion for an anion that would be pharmaceutically acceptable and therefore suitable for commercialisation, utilizing for example, reverse phase liquid chromatography as disclosed. Additionally, nicotinamide riboside is chemically labile, in particular under the chromatographic conditions used in the disclosed method. It is therefore proposed that the chromatographic conditions used could result in batches of less than optimum purity and, within the batches, great variability in terms of the side products produced. Another disadvantage is that careful control of the temperature of the reaction is necessary to minimise decomposition in the final stages of the synthesis of nicotinamide riboside, yet the disclosed method is exothermic and is therefore prone to microenvironment thermal fluctuation, especially in the event of large scale production set up.

Tanimori et al (S. Tanimori, T. Ohta and M. Kirihata, *Bioorganic & Medicinal Chemistry Letters*, 2002, 12, 1135-1137) and Franchetti et al (P. Franchetti, M. Pasqualini, R. Petrelli, M. Ricciutelli, P. Vita and L. Cappellacci, *Bioorganic & Medicinal Chemistry Letters*, 2004, 14, 4655-4658) also describe methods for the preparation of nicotinamide riboside. However, these methods also have the disadvantage of inevitably resulting in the preparation of the triflate salt by virtue of using TMSOTf as catalyst.

In summary, the disclosed methods have disadvantages which present obstacles to the scaling up of the method for commercial or industrial use, and which, therefore, greatly limit the commercial opportunities for the methods and the resultant compounds.

It is therefore an object of the invention to avoid or mitigate the disadvantages of the prior art.

It is also an object of the invention to provide a novel, useful and efficient method for the preparation of nicotinamide riboside and derivatives thereof.

It is also an object of the invention to provide a method for the preparation of nicotinamide riboside and derivatives thereof, whereby the method may be used to introduce a counter ion of choice to the prepared compounds, thereby producing compounds suitable for use as nutritional supplements or otherwise.

SUMMARY OF THE INVENTION

According to the present invention, there is provided a method of preparing a compound of formula (I)

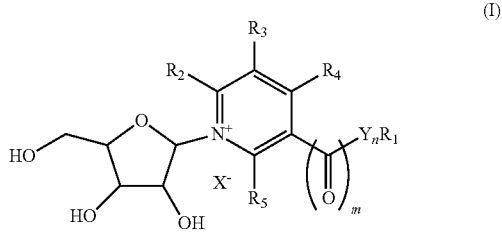

wherein
n is 0 or 1;
m is 0 or 1;
Y is O or S;
$R_1$ is selected from H, substituted or unsubstituted alkyl, substituted or unsubstituted alkenyl, substituted or unsubstituted alkynyl, substituted or unsubstituted aryl, substituted or unsubstituted primary or secondary amino, and substituted or unsubstituted azido;
$R_2$-$R_5$, which may be the same or different, are each independently selected from H, substituted or unsubstituted alkyl, substituted or unsubstituted alkenyl, substituted or unsubstituted alkynyl, and substituted or unsubstituted aryl; and
$X^-$ is an anion, selected from an anion of a substituted or unsubstituted carboxylic acid, a halide, a substituted or unsubstituted sulfonate, a substituted or unsubstituted phosphate, a substituted or unsubstituted sulfate, a substituted or unsubstituted carbonate, and a substituted or unsubstituted carbamate;
comprising reacting a compound of formula (II)

$$\text{(II)}$$

wherein n, m, Y and $R_1$-$R_5$ are as defined above;
with a compound of the formula $Z^+X^-$,
  wherein $X^-$ is as defined above, and
  wherein $Z^+$ is a N-containing cation;
in the presence of an aqueous solution and a carbon-containing catalyst;
to form the compound of formula (I).

Optionally, $Z^+$ is selected from a substituted or unsubstituted ammonium, a substituted or unsubstituted pyridinium, a substituted or unsubstituted pyrrolidinium, a substituted or unsubstituted imidazolium and a substituted or unsubstituted triazolium.

Optionally, $Z^+$ is a substituted or unsubstituted ammonium of the formula $N^+HR^IR^{II}R^{III}$, wherein $R^I$, $R^{II}$ and $R^{III}$, which may be the same or different, are each independently selected from H, substituted or unsubstituted alkyl, substituted or unsubstituted alkenyl, substituted or unsubstituted alkynyl, and substituted or unsubstituted aryl.

Optionally, $Z^+$ is an unsubstituted ammonium of the formula $NH_4^+$.

Optionally, $X^-$ is an anion of a substituted or unsubstituted carboxylic acid selected from an anion of a substituted or unsubstituted monocarboxylic acid and an anion of a substituted or unsubstituted dicarboxylic acid.

Optionally, $X^-$ is an anion of a substituted monocarboxylic acid, further optionally an anion of a substituted propanoic acid or an anion of a substituted acetic acid. Optionally, $X^-$ is an anion of substituted propanoic acid, further optionally an anion of a hydroxy propanoic acid, still further optionally an anion of 2-hydroxypropanoic acid, being lactic acid, the anion of lactic acid being lactate. Optionally, $X^-$ is an anion of a substituted acetic acid, being a substituted acetate, further optionally a trihaloacetate selected from trichloroacetate, tribromoacetate and trifluoroacetate. Still further optionally, the trihaloacetate is trifluoroacetate.

Optionally, $X^-$ is an anion of an unsubstituted monocarboxylic acid selected from formic acid, acetic acid, propionic acid and butyric acid, being formate, acetate, propionate and butyrate, respectively.

Optionally, $X^-$ is an anion of a substituted or unsubstituted amino-monocarboxylic acid or an anion of a substituted or unsubstituted amino-dicarboxylic acid. Further optionally, $X^-$ is an anion of an amino-dicarboxylic acid, optionally selected from glutamic acid and aspartic acid, being glutamate and aspartate, respectively.

Optionally, $X^-$ is an anion of ascorbic acid, being ascorbate.

Optionally, $X^-$ is a halide selected from chloride, bromide, fluoride and iodide, further optionally chloride or bromide.

Optionally, $X^-$ is a substituted or unsubstituted sulfonate. Further optionally, $X^-$ is a trihalomethanesulfonate selected from trifluoromethanesulfonate, tribromomethanesulfonate and trichloromethanesulfonate. Still further optionally, the trihalomethanesulfonate is trifluoromethanesulfonate.

Optionally, $X^-$ is a substituted or unsubstituted carbonate, further optionally hydrogen carbonate.

Optionally, $X^-$ is selected from chloride, acetate, formate, trifluoroacetate, ascorbate, aspartate, glutamate and lactate. Further optionally, $X^-$ is selected from chloride, acetate, formate and trifluoroacetate.

Optionally, the compound of the formula $Z^+X^-$ is selected from ammonium chloride, ammonium acetate, ammonium formate, ammonium trifluoroacetate, ammonium ascorbate, ammonium aspartate, ammonium glutamate and ammonium lactate. Further optionally, the compound of the formula $Z^+X^-$ is selected from ammonium chloride, ammonium acetate, ammonium formate and ammonium trifluoroacetate.

Optionally, the compound of formula (II) and the carbon-containing catalyst are present in a respective molar ratio of from about 10:1 to about 1:10, optionally from about 5:1 to about 1:5, further optionally from about 4:1 to about 1:4, still further optionally about 1:1 or 1:2 or 1:3 or 1:4.

Suitable carbon-containing catalysts include, but are not limited to, activated charcoal or graphite.

As used herein, the term "activated charcoal" is intended to mean a carbon containing material processed to be highly porous thereby increasing the surface area of the material. The term "activated charcoal" is intended to be synonymous with the term "activated carbon". The activated charcoal may be in the form of powders and/or fibres and/or granules and/or pellets. Optionally, the activated charcoal may act as a support for a metal. Suitable metals include, but are not limited to, transition metals. Suitable transition metals include, but are not limited to the platinum group metals, optionally selected from ruthenium, rhodium, palladium, osmium, iridium, and platinum, or a combination thereof.

Optionally, the aqueous solution consists essentially of water.

Optionally, the aqueous solution comprises, in addition to water, an organic solvent.

Suitable organic solvents include, but are not limited to, substituted or unsubstituted ethers, substituted or unsubstituted esters, substituted or unsubstituted ketones, substituted or unsubstituted aliphatic or aromatic hydrocarbons, and combinations thereof.

Optionally, the organic solvent, when present, comprises an ether selected from diethyl ether, methyl tert-butyl ether, ethyl tert-butyl ether, di-tert-butyl ether, diisopropyl ether, dimethoxymethane, tetrahydrofuran, 2-methyltetrahydrofuran, and tetrahydropyran, or a combination thereof.

Optionally, the organic solvent, when present, comprises an ester selected from methyl acetate, ethyl acetate, isopropyl acetate, n-propyl acetate, isobutyl acetate and n-butyl acetate, or a combination thereof.

Optionally, the organic solvent, when present, comprises a ketone selected from methyl isobutyl ketone and methyl isopropyl ketone, or a combination thereof.

Optionally, the organic solvent, when present, comprises an unsubstituted aliphatic hydrocarbon solvent selected from pentane, hexane, cyclohexane and heptane, or a combination thereof.

Optionally, the organic solvent, when present, comprises a substituted aliphatic hydrocarbon solvent, optionally a halogenated aliphatic hydrocarbon solvent, further optionally a chlorinated aliphatic hydrocarbon solvent selected from dichloromethane, trichloromethane, tetrachloromethane, 1,2-chloroethane, 1, 1, 1-trichloroethane and trichloroethylene, or a combination thereof.

Optionally the organic solvent, when present, comprises an aromatic hydrocarbon solvent selected from benzene, toluene, ethylbenzene and xylene, or a combination thereof.

Optionally, the aqueous solution comprises water and organic solvent in a respective ratio by volume of from about 1:5 to about 5:1, optionally from about 1:3 to about 3:1, further optionally from about 1:2 to about 2:1, still further optionally about 1:1.

Optionally, the reaction is carried out in a pH range of from about 6 to about 8, optionally from about 6.5 to about 7.5.

Optionally, the reaction is carried out at a temperature of from about 10° C. to about 40° C., optionally from about 15° C. to about 35° C., further optionally from about 15° C. to about 30° C., still further optionally from about 15° C. to about 20° C., even further optionally from about 20° C. to about 25° C., even further optionally at a temperature of about 20° C. or 21° C. or 22° C. or 23° C. or 24° C. or 25° C.

Optionally, the reaction is carried out for a period of time of from about 1 minute to about 180 minutes, optionally, from about 2 minutes to about 120 minutes, further optionally from about 5 minutes to about 120 minutes, still further optionally from about 10 minutes to about 120 minutes, even further optionally from about 20 minutes to about 120 minutes, even further optionally from about 30 minutes to about 120 minutes, still further optionally from about 60 minutes to about 120 minutes, even further optionally from about 60 minutes to about 90 minutes, still further optionally about 60 minutes or 70 minutes or 80 minutes.

Optionally, the method further comprises a filtration step to remove the carbon-containing catalyst from the prepared compound of formula (I). Suitable filtration means for use in the filtration step include, but are not limited to, syringe filters and/or paper filters, and/or any inert, insoluble substance capable of acting as a filter, e.g. alumina and/or silica and/or diatomaceous earth. It will be appreciated any other suitable filtration means may be used.

As used herein, the term "substituted" is intended to mean that any one or more hydrogen atoms is replaced with any suitable substituent, provided that the normal valency is not exceeded and the replacement results in a stable compound. Suitable substituents include, but are not limited to, alkyl, alkylaryl, aryl, heteroaryl, halide, hydroxyl, carboxylate, carbonyl (including alkylcarbonyl and arylcarbonyl), phosphate, amino (including alkylamino, dialkylamino, hydroxylamino, dihydroxylamino, alkyl hydroxylamino, arylamino, diarylamino and alkylarylamino), thiol (including alkylthiol, arylthiol and thiocarboxylate), sulfate, nitro, cyano and azido.

As used herein, the term "alkyl" is intended to mean a substituted or unsubstituted, saturated or unsaturated, optionally saturated, linear, branched or cyclic, aliphatic hydrocarbon, having from 1 to 12 carbon atoms, optionally from 1 to 10 carbon atoms, further optionally from 1 to 8 carbon atoms, still further optionally from 1 to 6 carbon atoms, even still further optionally 1 or 2 or 3 or 4 or 5 carbon atoms. Suitable alkyls include, but are not limited to, methyl, ethyl, n-propyl, iso-propyl, n-butyl, iso-butyl, tert-butyl, n-pentyl, iso-pentyl, n-hexyl, iso-hexyl, cyclopropyl, cyclobutyl, cyclopentyl and cyclohexyl. Optionally, when Y is O, n is 1, and m is 1, ethyl is preferred.

As used herein, the term "alkenyl" is intended to mean a substituted or unsubstituted, linear, branched or cyclic, aliphatic hydrocarbon, having at least one carbon-carbon double bond, and having from 2 to 12 carbon atoms, optionally from 2 to 10 carbon atoms, further optionally from 2 to 8 carbon atoms, still further optionally from 2 to 6 carbon atoms, even still further optionally 2 or 3 or 4 or 5 carbon atoms. Suitable alkenyl groups include, but are not limited to, ethenyl, propenyl and butenyl, As used herein, the term "alkynyl" is intended to mean a substituted or unsubstituted, linear, branched or cyclic, aliphatic hydrocarbon, having at least one carbon-carbon triple bond, and having from 2 to 12 carbon atoms, optionally from 2 to 10 carbon atoms, further optionally from 2 to 8 carbon atoms, still further optionally from 2 to 6 carbon atoms, even still further optionally 2 or 3 or 4 or 5 carbon atoms. Suitable alkynyl groups include, but are not limited to, ethynyl, propynyl, butynyl, and the like.

As used herein, the term "aryl" is intended to mean a substituted, unsubstituted, monocyclic or polycyclic, aromatic hydrocarbon. Suitable aryls include, but are not limited to, substituted or unsubstituted phenyl, and substituted or unsubstituted heteroaryl.

Optionally, the substituted or unsubstituted primary or secondary amino is selected from substituted or unsubstituted alkylamino, substituted or unsubstituted dialkylamino, substituted or unsubstituted hydroxylamino, substituted or unsubstituted dihydroxylamino, and substituted or unsubstituted alkyl hydroxylamino.

Optionally, the substituted or unsubstituted azido is selected from substituted or unsubstituted alkyl azido and substituted or unsubstituted aryl azido.

It will be appreciated that, when n is 0 and m is 0, $R_1$ is directly attached to the pyridine ring or to the pyridinium ring, as appropriate.

Optionally, in an embodiment of formula (I), n is 0, m is 1, $R_1$ is $NH_2$, $R_2$-$R_5$ are each H, and $X^-$ is selected from chloride, acetate, formate and trifluoroacetate.

Optionally, in an embodiment of formula (II), n is 0, m is 1, $R_1$ is $NH_2$, and $R_2$-$R_5$ are each H.

Optionally, the compound of formula (II) and the compound of the formula $Z^+X^-$ are present in a respective molar ratio of from about 1:5 to about 5:1, optionally from about 1:3 to about 3:1, further optionally from about 1:2 to about 2:1, still further optionally about 1:1.

Optionally, the method comprises stirring the reactants, optionally using a magnetic or mechanical stirrer, further optionally an overhead mechanical stirrer.

In an embodiment, the carbon-containing catalyst used in the preparation of a compound of formula (I) may be provided in the form of an activated charcoal column, for example an activated charcoal material such as those supplied by Sigma Aldrich under the trade names NORIT (Trade Mark) or DARCO (Trade Mark), or from CarboChem, W Lancaster Ave, Ardmore, PA 19003, USA, or a carbon supported catalyst in a CatCart Packer (Trade Mark) column from ThalesNano, Graphisoft Park, Záhony u. 7. H-1031 Budapest, Hungary. In this embodiment, the activated charcoal column may be used as part of any suitable liquid chromatography system, including, but not limited to, a fast protein liquid chromatography (FPLC) or a high performance liquid chromatography (HPLC) system, or a flow chemistry system, such as the ThalesNano (Trade Mark) H-cube systems and related flow reactors, available from ThalesNano, details provided above. In this case, the reactants would be recirculated onto the column in a continuous manner until the compound of formula (II) is no longer detected by UV at 340 nm.

Optionally, the compound of formula (II) is prepared by reacting a compound of formula (III)

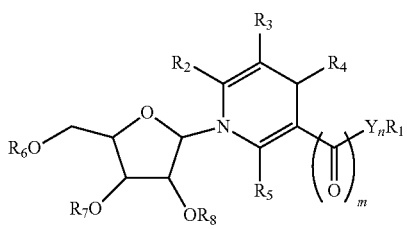

(III)

wherein
n, m, Y and $R_1$-$R_5$ are as defined above; and
$R_6$, $R_7$ and $R_8$, which may be the same or different, are each independently a hydroxyl-protecting group;
with a deprotecting agent;
to form the compound of formula (II).

Suitable $R_6$, $R_7$ and $R_8$ moieties include, but are not limited to, ester-type protecting groups, ether-type protecting groups, and silyl-type protecting groups.

As used herein, the term "ester-type protecting group" is intended to mean a protecting group that forms an ester bond for the purpose of hydroxyl protection and which may be substituted or unsubstituted. Suitable ester-type protecting groups include, but are not limited to, acetyl, propionyl, isopropionyl, benzoyl, and trihaloacetyl, optionally trifluoroacetyl or trichloroacetyl.

As used herein, the term "ether-type protecting group" is intended to mean a protecting group that forms an ether bond for the purpose of hydroxyl protection and which may be substituted or unsubstituted. Suitable ether-type protecting groups include, but are not limited to, benzyl, p-methoxybenzyl, methoxymethyl and allyl ethers.

As used herein, the term "silyl-type protecting group" refers to a protecting group that forms a silyloxy bond for the purpose of hydroxyl protection. Examples thereof from trimethylsilyl, triethylsilyl, triisopropylsilyl, 2-(trimethylsilyl)ethoxymethyl, tert-butyldimethylsilyl, tert-butyldiphenylsilyl and tetraisopropyldisilyl.

Optionally, the $R_6$, $R_7$ and $R_8$ moieties are selected from substituted and unsubstituted acetyl, and substituted and unsubstituted benzoyl.

Optionally, at least two of $R_6$, $R_7$ and $R_8$ are selected from unsubstituted acetyl or unsubstituted benzoyl.

Optionally the deprotecting agent is an acid or a base. Deprotection can also be achieved by catalytic hydrogenation (Pd/C; $H_2$) for the aromatic ether protecting groups and by fluoride-catalysed chemistry (e.f. TBAF in THF) for all the silyl ethers. Optionally, when $R_6$, $R_7$ and $R_8$ each comprise unsubstituted acetyl or unsubstituted benzoyl, the deprotecting agent is a base, optionally selected from $NH_3$, $Na_2CO_3$ and NaOH. It will be appreciated by a skilled person that any other conventional deprotecting agent may be used.

Optionally, the reaction is carried out in the presence of a protic or aprotic solvent or a combination thereof.

Suitable protic solvents include, but are not limited to, water, substituted or unsubstituted alcohol, or a combination thereof. Suitable substituted alcohols include substituted or unsubstituted fluorinated alcohols. Suitable unsubstituted alcohols include methanol, ethanol and propanol, optionally methanol.

Suitable aprotic organic solvents include, but are not limited to, substituted or unsubstituted ethers, substituted or unsubstituted esters, substituted or unsubstituted ketones, substituted or unsubstituted aliphatic or aromatic hydrocarbons, and combinations thereof, as defined above.

Optionally, the reactants are subjected to mechanical grinding, further optionally using a ball milling or planetary ball milling machine.

Optionally, in an embodiment of formula (III), n is 0, m is 1, $R_1$ is $NH_2$, $R_2$-$R_5$ are each H, and $R_6$-$R_8$ are each acetyl.

Further optionally, in another embodiment of formula (III), n is 1, Y is O, m is 1, $R_1$ is ethyl, $R_2$-$R_5$ are each H, and $R_6$-$R_8$ are each acetyl.

Still further optionally, in another embodiment of formula (III), n is 0, m is 1, $R_1$ is $NH_2$, $R_2$-$R_5$ are each H, and $R_6$-$R_8$ are each benzoyl.

Optionally, the compound of formula (III) is prepared by reacting a compound of formula (IV)

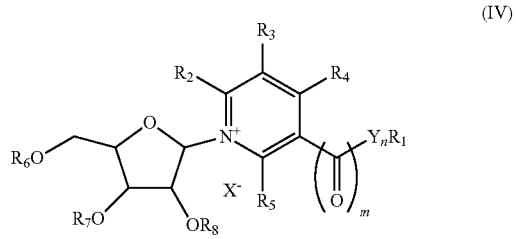

(IV)

wherein
n, m, Y, $R_1$-$R_8$ and $X^-$ are as defined above;
with a reducing agent,
an aqueous solution
and an organic solvent
to form a compound of formula (III).

Optionally, $X^-$ is selected from ascorbate, glutamate, aspartate, lactate and acetate.

Suitable organic solvents are as defined above in respect of the preparation of a compound of formula (I) from formula (II).

Optionally, when at least two of $R_6$, $R_7$ and $R_8$ comprise unsubstituted acetyl, the organic solvent is selected from dichloromethane, 1,2-chloroethane, n-butyl acetate, chloroform and ethyl acetate, or a combination thereof, further optionally ethyl acetate.

Optionally, when at least two of $R_2$, $R_3$ and $R_4$ comprise unsubstituted benzoyl, the organic solvent is selected from trichloroethylene, carbon tetrachloride, diisopropyl ether, toluene, methyl tert-butyl ether, benzene and diethyl ether, or a combination thereof, further optionally diethyl ether.

Optionally, the reducing agent is selected from sodium dithionite or sodium borohydride.

Optionally, the method may comprise the simultaneous addition of the reducing agent, aqueous solution and organic solvent; or the sequential addition of the reducing agent, aqueous solution and organic solvent, in any order; or a combination thereof.

Optionally, the aqueous solution consists essentially of water.

It will be appreciated that, optionally, the aqueous solution and the organic solvent form a bi-phasic solution comprising an aqueous phase and an organic phase.

Optionally, the method comprises the additional steps of
separating the organic phase from the aqueous phase; and
extracting the compound of formula (III) from the organic solvent.

It will be appreciated by a skilled person that the hydroxyl protecting groups $R_6$, $R_7$ and $R_8$, are required to be lipophilic to the extent that the reduced compound of formula (III), once prepared, migrates into the organic phase of the biphasic reaction medium formed by the aqueous solution (aqueous phase) and organic solvent (organic phase).

Optionally, the reactants are subjected to mechanical grinding, further optionally using a ball mill or planetary ball milling machine.

Optionally, in an embodiment of formula (IV), n is 0, m is 1, $R_1$ is $NH_2$, $R_2$-$R_5$ are each H, $R_6$-$R_8$ are each acetyl, and $X^-$ is $^-OTf$.

Further optionally, in another embodiment of formula (III), n is 1, Y is O, m is 1, $R_1$ is ethyl, $R_2$-$R_5$ are each H, $R_6$-$R_8$ are each acetyl, and $X^-$ is $^-OTf$.

Still further optionally, in another embodiment of formula (III), n is 0, m is 1, $R_1$ is $NH_2$, $R_2$-$R_5$ are each H, and $R_6$-$R_8$ are each benzoyl, and $X^-$ is $^-OTf$.

According to the invention, there are also provided compounds derivable from the methods disclosed herein.

Accordingly to the invention, there is further provided a compound of formula (I)

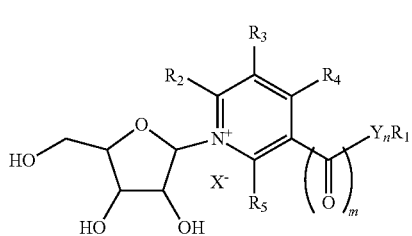

(I)

wherein
n, m, Y, $R_1$-$R_5$ and $X^-$ are as defined above.

Optionally, $X^-$ is selected from acetate, formate and trifluoroacetate.

Optionally, the compound of formula (I) has the formula (IA), i.e. is the β-anomer,

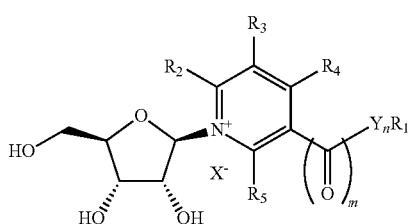

(IA)

wherein
n, m, Y, $R_1$-$R_5$ and $X^-$ are as defined above.

Optionally, the compound of formula (II) has the formula (IIA), i.e. is the β-anomer,

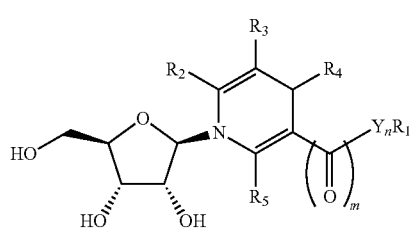

(IIA)

wherein
n, m, Y and $R_1$-$R_5$ are as defined above.

Optionally, the compound of formula (III) has the formula (IIIA), i.e. is the β-anomer,

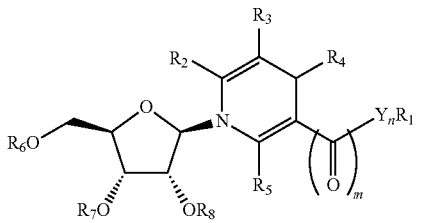

(IIIA)

wherein
n, m, Y and $R_1$-$R_8$ are as defined above.

Optionally, the compound of formula (IV) has the formula (IVA), i.e. is the β-anomer,

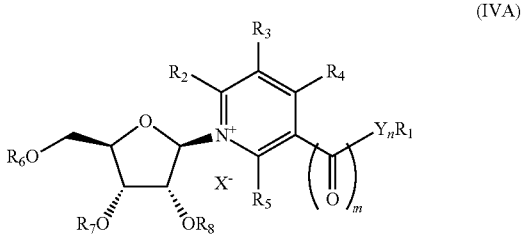

(IVA)

wherein
n, m, Y, $R_1$-$R_8$ and $X^-$ are as defined above.

Advantages of the invention include, but are not limited to the following:

(1) The preparation of compounds of formula (I) from compounds of formula (II) provides an efficient method of introducing a counter ion of choice for nicotinamide riboside and its derivatives. Starting from a compound of formula (II), e.g. reduced NRH, a desired counter ion may be introduced. Furthermore, even if the method starts by using compounds of formula (IV) in the form of the triflate salt, the methods of the invention enable the triflate anion to be exchanged during the method in a simple and efficient manner, to a counter ion of choice. Thus, the disclosed methods conveniently enable the preparation of compounds having potential use as nutritional supplements or otherwise.

(2) The invention provides stereoselective methods for the preparation of nicotinamide riboside and derivatives thereof, producing the desired β-anomer. This is in contrast, for example, to Tanimori et al, which is not stereoselective and produces significant amounts of the α-anomer, which is undesirable. Additionally, the methods of the invention are useful, efficient, and can be easily scaled up for industry and commercialisation, and provide for the minimisation of solvent use, purification and reaction time. For example, the methods of the invention for preparing compounds of formula (I) from compounds of formula (II), are conveniently completed in less than 2 hours with quantitative yields. The methods for the preparation of compounds of formula (I) starting from compounds of formula (IV) are also very efficient and produce very good yields. The methods may conveniently be carried out at room temperature.

(3) The methods described herein are capable of preparing not just nicotinamide riboside but also a whole range of derivatives, which is not disclosed in either Tanimori et al or Franchetti et al. The derivatives include not just derivatives of nicotinamide riboside but also the reduced form of nicotinamide riboside and derivatives thereof. Furthermore, although not described herein, a skilled person will appreciate that, starting from compounds of formula (II), it is possible to easily access the phosphorylated parents of nicotinamide riboside and derivatives thereof, for example nicotinamide mononucleotide and nicotinate mononucleotide.

(4) The protecting groups used in the preparation of compounds of formula (III) from compounds of formula (IV) may advantageously be chosen to be sufficiently lipophilic so that they facilitate the migration of the compounds of formula (III) into the organic phase of the reaction medium, for ease of extraction.

(5) The methods described herein conveniently use reactants which enable the compounds of formula (I) to be prepared in a neutral pH range of from about 6 to about 8. For example, in the preparation of the compounds of formula (I) from the compounds of formula (II), this neutral pH range enables both the starting materials (compounds of formula (II)), which are acid labile, and the final products (compounds of formula (I)), which are base labile, to be stable during the reaction.

(6) The inventors have surprisingly found that, the use of a N-containing cation as $Z^+$ (the proton source), conveniently enables the efficient preparation of compounds of formula (I) from compounds of formula (II) in quantitative yield, and, as mentioned in point (5), in a neutral pH range. Without wishing to be bound by theory, it is proposed that $Z^+$, the proton source, must be a conjugated acid of an organic base which is protonated in an equilibrated manner within the neutral pH range. The inventors propose that, by using a N-containing cation as the proton source $Z^+$, the N atom of the proton source has a pKa greater than the pKa of the N atom of the dihydropyridine of the compound of formula (II). Therefore, in simple terms, due to the relative pKa values, the N atom of the proton source $Z^+$ (i.e. N—$H^+$) holds onto the proton $H^+$ until after the N atom of the dihydropyridine has been oxidised (which oxidation, the inventors propose, is facilitated by the carbon-containing catalyst). It is only after the N atom of the dihydropyridine has been oxidised that it will be protonated by the proton source $Z^+$. The inventors propose that if a proton source other than one containing a N atom is used, for example a phosphonium cation containing P—$H^+$ or a sulfonium cation containing S—$H^+$, it is proposed that such proton sources would cause the pH of the reaction medium to fall below the neutral pH range, and the proton sources would release their protons in this lower pH range. It is proposed that this change would cause the N atom of the dihydropyridine to be protonated before oxidation, thereby resulting in the undesirable hydrolysis of a C—N bond of the dihydropyridine. It is also proposed that this resultant instability of the dihydropyridine due to the undesirable breaking of a C—N bond, would also occur using a weak acid (e.g. carboxylic acid) or a strong acid (e.g. hydrochloric acid, phosphoric acid or sulphuric acid). Thus, it is proposed that only a N-containing cation as proposed, is capable of releasing a proton in a pH range (neutral) which allows the reaction to proceed as desired to form the compounds of formula (I) from the compounds of formula (II).

THE EXAMPLES

Figure 2:
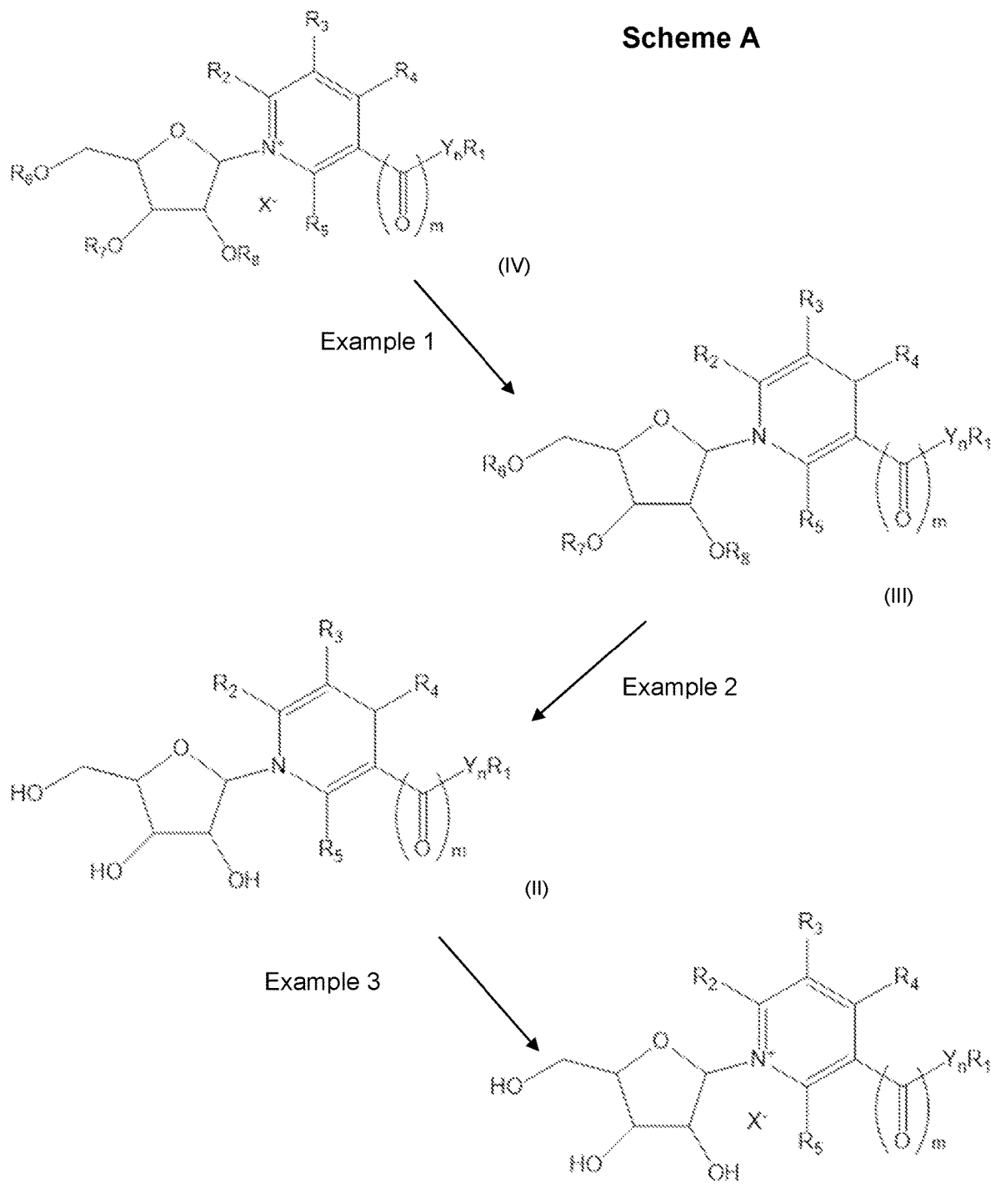
Figure 3:
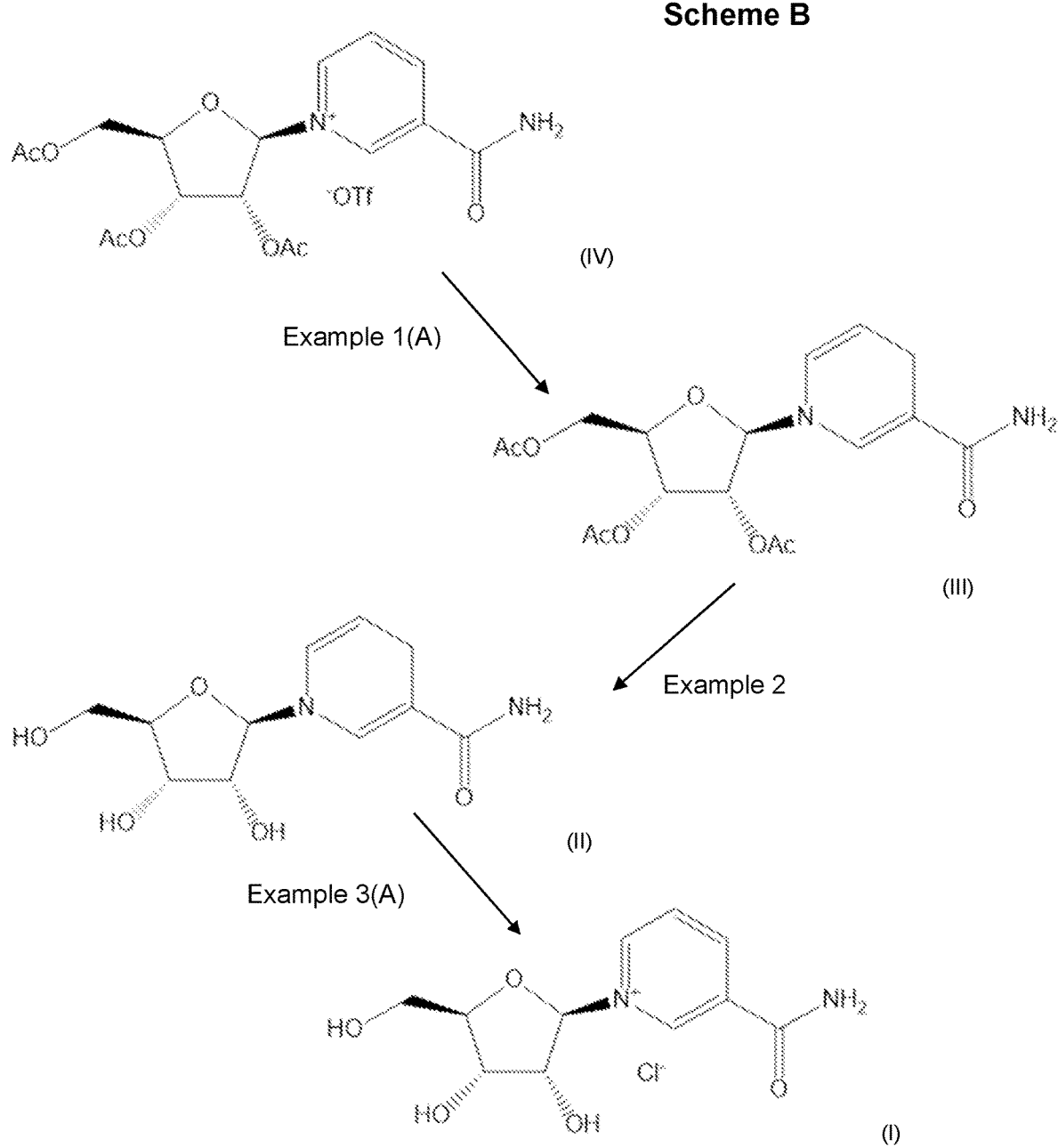
Figure 4:
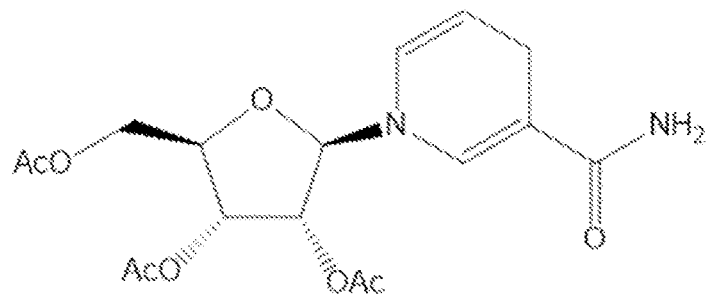
Figure 4:
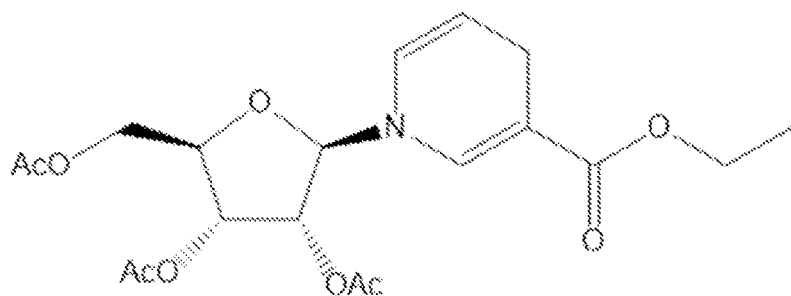
Figure 4:
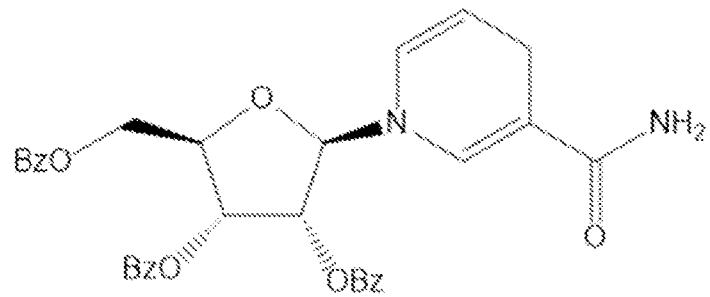
Figure 4:
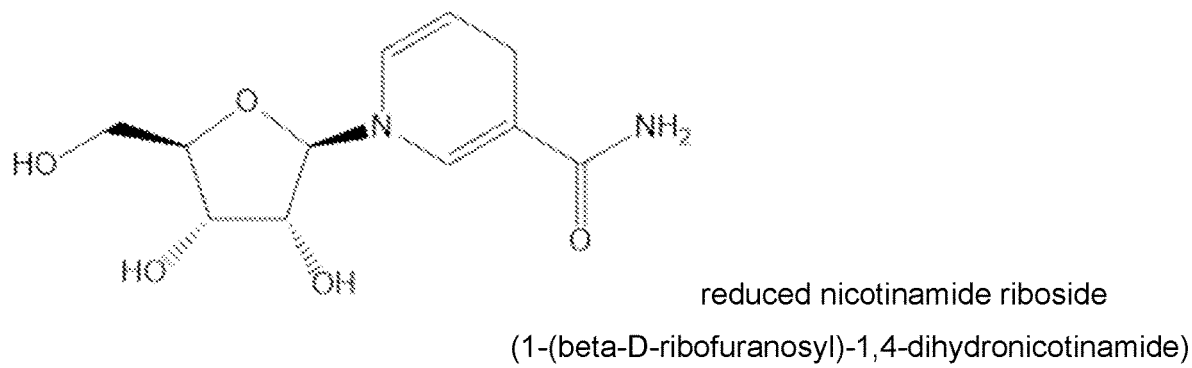
Figure 5:
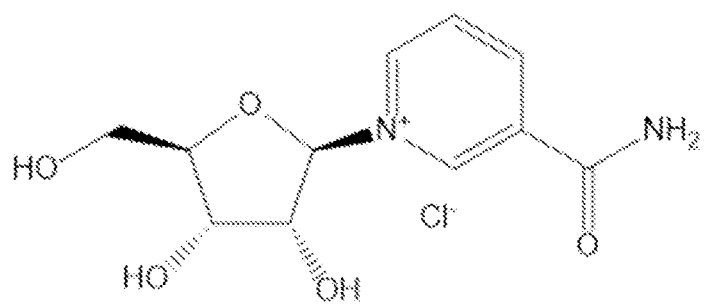
Figure 5:
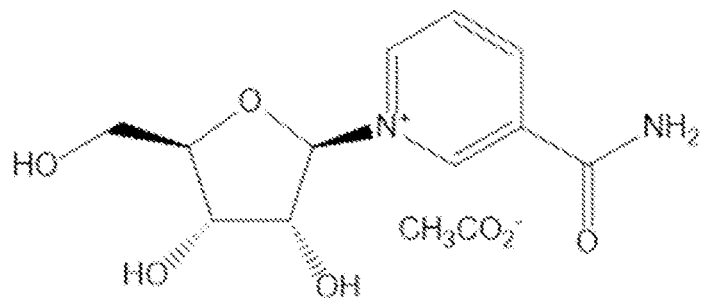
Figure 5:
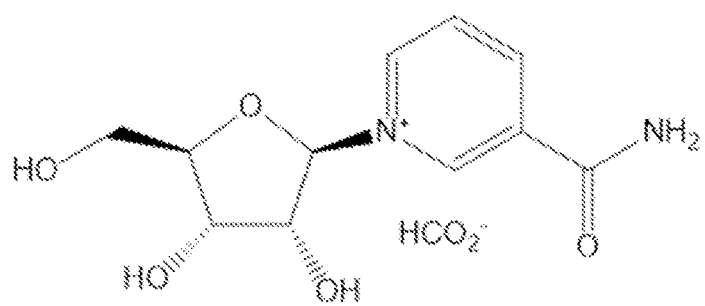
Figure 5:
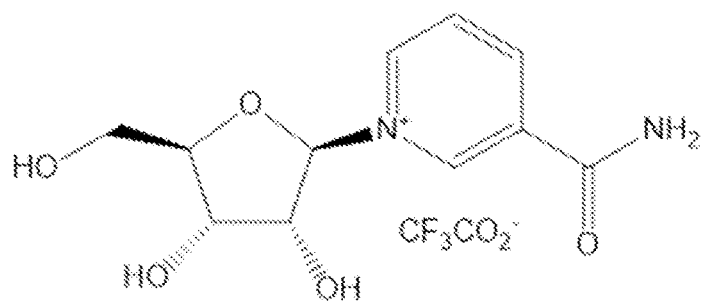

Embodiments of the present invention will now be described, with reference to the accompanying, non-limiting examples and drawings, in which:

FIG. 1 shows the β-anomer forms of nicotinamide riboside, nicotinate riboside, nicotinamide mononucleotide and nicotinate mononucleotide, without counter ions;

FIG. 2 depicts Scheme A, which is a scheme illustrating, in general terms, that compounds of formula (IV) may be used to prepare compounds of formula (III), as described in Example 1; that compounds of formula (III) may be used to prepare compounds of formula (II), as described in Example 2; and that compounds of formula (II) may be used to prepare compounds of formula (I), as described in Example 3; wherein n, m, Y, $R_1$-$R_8$ and $X^-$ are as defined above;

FIG. 3 depicts Scheme B, which is a scheme illustrating, in general terms, that triacetyl nicotinamide riboside, triflate salt may be used to prepare triacetyl-1,4-dihydronicotinamide riboside, as described in Example 1(A), and that triacetyl-1,4-dihydronicotinamide riboside may be used to prepare 1-(beta-D-ribofuranosyl)-1,4-dihydronicotinamide, as described in Example 2, and that 1-(beta-D-ribofuranosyl)-1,4-dihydronicotinamide may be used to prepare nicotinamide riboside, chloride salt, as described in Examples 3(A), 3(E) and 3(F). The β-anomers of all of the mentioned compounds are shown. It will be appreciated that Scheme B is merely exemplary and is not to be construed as limiting the invention thereto;

FIG. 4 shows the β-anomer forms of triacetyl-1,4-dihydronicotinamide riboside (Example 1(A)), triacetyl O-ethyl-1,4-dihydronicotinate riboside, (Example 1(B)), tribenzoyl-1,4-dihydronicotinamide riboside (Example 1(C)), and 1-(beta-D-ribofuranosyl)-1,4-dihydronicotinamide (Example 2); and FIG. 5 shows the β-anomer forms of nicotinamide riboside, chloride salt (Examples 3(A), 3(E) and 3(F)), nicotinamide riboside, acetate salt (Example 3(B)), nicotinamide riboside, formate salt (Example 3(C)), and nicotinamide riboside, trifluoroacetate salt (Example 3(D)).

EXAMPLE 1

Compounds of formula (III) were prepared in accordance with the invention as follows. The pH of the reaction media described in the following examples was in the region of about 6-8.

Example 1(A): Preparation of Reduced Triacetyl Nicotinamide Riboside, Namely triacetyl-1,4-dihydronicotinamide riboside, a Compound of Formula (III) (the β-Anomer Form of which is Shown in FIG. 4)

Reduction: All solvents were degassed prior to use by sonication and argon bubbling. Sodium dithionite (0.656 g, 3.76 mmol, 2 eq) and sodium hydrogencarbonate (0.79 g, 9.40 mmol, 5 eq) were added to a clean, dry round bottom flask with a magnetic stirrer and placed under inert atmosphere. A compound of formula (IV), namely triacetyl nicotinamide riboside, triflate ($CF_3SO_3^-$, also known as —OTf) salt (1 g, 1.88 mmol, 1 eq) was then dissolved in a minimum amount of water (<10 ml) and slowly added to the reaction vessel. Once the reaction settled, further water was added to the reaction until all of the reactants had dissolved (<10 ml) and was left to stir for 20 minutes. The aqueous solution was then extracted with three half portions of dichloromethane (DCM). The DCM fractions were collected and concentrated under reduced pressure, affording the triacetyl-1,4-dihydronicotinamide riboside derivative (triacetyl-NRH) with residual amounts of starting material (<5%). The aqueous layer was subjected to the above conditions a second time to increase yields which averaged 65%. Ethyl acetate was also an excellent alternative extraction solvent in place of DCM, yielding a 75% yield.

$^1$H-NMR (MeOD, 400 MHz) –δ7.15 (s, 1H, H-5), 5.95 (d, 1H, J=7.21 Hz, H-6), 5.25 (d, 1H, J=2.84 Hz) & 5.17 (d, 1H, J=1.80 Hz) (H-8 & H-7), 4.96 (d, 1H, J=7.09 Hz, H-4), 4.87 (ABX, 1H, Jaa=8.18 Hz, Jab=3.60 Hz, H-9), 4.26 (d, 2H, J=3.20 Hz, H-10 & H-10) 4.19 (m, 1H, J=3.00 Hz, H-3), 3.13 (m, 2H, J=1.18 Hz, H-2), 2.13 (s, 3H), 2.11 (s, 3H), 2.10 (s, 3H) (H-13, H-15, H-17). 13C-NMR (MeOD, 125 MHz) –δ172.80 (C-11), 170.40 (C-12, C-14, C-16), 137.90 (C-5), 125.20 (C-4), 105.12 (C-6), 95.24 (C-3), 83.49 (C-9), 71.18 (C-8), 70.26 (C-7), 61.55 (C-10), 22.16 (C-2), 21.52 (C-13, C-15, C-17). HMRS m/z: 383.1445; Calc. Mass: 383.1454.

The compound of formula (IV), namely triacetyl nicotinamide riboside, triflate (—OTf) salt was prepared as follows. Nicotinamide (10 g, 81.89 mmol, 1 eq) was silylated using TMSCl (15.6 ml, 122.85 mmol, 1.5 eq) in HMDS (100 ml) at 130° C. in quantitative yield, in order to force the β-selectivity via the following Vorbrüggen reaction. Ribose tetraacetate (also known as tetraacetate riboside) was reacted with the resultant silylated nicotinamide in the presence of 5 equivalents of TMSOTf. The reactants were shaken in a 1.5 ml steel vessel with a 5 mm diameter steel ball bearing in a Retsch MM400 mixer mill at 25 Hz for 0.5 h. At this point the formed triacetylated nicotinamide riboside (compound of formula (IV)) could be isolated. It will be appreciated that the triacetyl nicotinamide riboside is not limited to being produced by this exact method, and could, for example, be produced using a conventional Vorbrüggen reaction as described, for example, in International PCT patent publication no. WO 2007/061798 or in T. Yang, N. Y. K. Chan and A. A. Sauve, *Journal of Medicinal Chemistry*, 2007, 50, 6458-6461.

$^1$H-NMR (MeOD, 400 MHz) –δ 9.61 (s, 1H, aromatic), 9.30 (dt, 1H, J=6.3, 1.4 Hz, aromatic), 9.10 (dt, 1H, J=8.2, 1.4 Hz, aromatic), 8.37 (dH, 1H, J=8.2, 6.3 Hz, aromatic), 6.60 (d, 1H, J=3.9 Hz, H-1 (anomeric)), 5.60 (dd, 1H, J=5.6, 3.9 Hz, H-2), 5.46 (t, 1H, J=5.6 Hz, H-3), 4.81-4.84 (m, 1H, H-4), 4.61 (ABX, 1H, $J_{a,a'}$=13.1 Hz, $J_{a,b}$=3.5 Hz, H-5), 4.51 (ABX, 1H, $J_{a,a'}$=13.0 Hz, $J_{a,b}$=2.8 Hz, H-5'), 2.20 (s, 3H, OAc), 2.17 (s, 3H, OAc), 2.16 (s, 3H, OAc).

$^{13}$C-NMR (MeOD, 125 MHz) –δ 172.1, 171.6, 171.2 (3× C=OCH$_3$), 164.9 (C=ONH$_2$) 147.0, 144.3, 142.3, 136.2, 129.6, (aromatic), 121.6 (q, J=320.2 Hz, CF$_3$), 99.4 (C-1 (anomeric)), 84.4 (C-4), 77.6 (C-2), 70.7 (C-3), 63.5 (C-5), 20.7 (OAc), 20.3 (OAc), 20.2 (OAc).

$^{19}$F-NMR (MeOD, 376 MHz) –δ–79.9 (triflate counterion)

Example 1(B): Preparation of Reduced Triacetyl Nicotinate Ester Riboside, Namely Triacetyl O-ethyl-1,4-dihydronicotinate riboside, a Compound of Formula (III) (the β-Anomer Form of which is Shown in FIG. 4)

Reduction: A compound of formula (IV), namely triacetyl O-ethyl nicotinate riboside, triflate (—OTf) salt (2.30 g, 4.2 mmol, 1 eq) was dissolved in 20 mL H$_2$O and a solution of a solution of NaHCO$_3$ (1.77 g, 21.0 mmol, 5 eq) and sodium dithionite (1.47 g, 8.22 mmol, 2 eq) in 30 mL H$_2$O was added and stirred for 2 hrs. The yellow solution obtained was then washed with 2× ethyl acetate (EtOAc, 40 mL), the organic layer dried over MgSO$_4$, filtered and concentrated to provide 900 mg (39% yield) of 2,3,5-triacetyl O-ethyl-1,4-dihydronicotinate riboside (a yellow oil) without further purification. 80% purity based on $^1$H-NMR.

$^1$H-NMR-δ 7.27 (1H, s, H-6), 6.05 (1H, dd, J=8.2, 1.5 Hz, H-7), 5.26 (1H, dd, J=5.8, 2.8 Hz, H-3), 5.23 (1H, dd, J=6.9, 5.8 Hz, H-2), 5.08 (1H, d, J=6.9 Hz, H-1), 4.91 (1H, dt, J=8.3, 3.5 Hz, H-8), 4.24-4.30 (3H, m, H-4, H-5, H-5'), 4.11 (2H, q, J=7.2 Hz, H-11), 3.04-3.06 (2H, m, H-9), 2.16 (3H, s, OAc), 2.12 (3H, s, OAc), 2.09 (3H, s, OAc), 1.25 (3H, t, J=7.2 Hz, H-12).

$^{13}$C-NMR-δ 172.2, 171.5, 171.3, 169.8, (3× C=O—CH$_3$ and C=O—OEt), 139.9 (C-6), 126.3 (C-7), 106.4 (C-8), 101.5 (C-10), 94.2 (C-1), 80.4 (C-4), 72.3 (C-2), 72.1 (C-3), 64.8 (C-5), 61.0 (C-11), 23.4 (C-9), 20.7, 20.5, 20.3 (3× C=O—CH$_3$), 14.8 (C-12).

The compound of formula (IV), namely triacetyl O-ethyl nicotinate riboside, triflate (—OTf) salt was prepared as follows. Ribose tetraacetate (also known as tetraacetate riboside) was reacted with ethyl nicotinate (Sigma Aldrich) using the general ball milling Vorbrüggen procedure described in Example 1(A) above. The reactants, namely leg tetraacetate riboside, leg TMSOTf, leg ethyl nicotinate, were reacted for 30 mins in a 1.5 ml steel vessel with a 1.5 cm diameter steel ball bearing in a Retsch MM400 mixer mill at 25 Hz. The crude reaction mixture (containing some unreacted ethyl nicotinate and starting sugar, <10%) was used for the reduction step (described above) without further purification. It will be appreciated that the triacetyl O-ethyl nicotinate riboside, triflate (—OTf) salt is not limited to being produced by this exact method, and could, for example, be produced using a conventional Vorbrüggen reaction as described, for example, in International PCT patent publication no. WO 2007/061798 or in T. Yang, N. Y. K. Chan and A. A. Sauve, *Journal of Medicinal Chemistry*, 2007, 50, 6458-6461.

$^1$H-NMR (D$_2$O, 400 MHz) –δ 9.45 (s, 1H, aromatic), 9.14 (d, 1H, J=6.1 Hz, aromatic), 9.02 (d, 1H, J=7.8 Hz, aromatic), 8.18 (t, 1H, J=6.7 Hz, aromatic), 6.51 (d, 1H, J=4.1 Hz, H-1 (anomeric)), 5.47 (t, 1H, J=4.4 Hz, H-2), 5.36 (t, 1H, J=4.7 Hz, H-3), 4.81-4.84 (m, 1H, H-4), 4.45-4.48 (m, 2H, H-5), 4.36 (q, 2H, J=7.0 Hz, C=OCH$_2$CH$_3$), 2.04 (s, 3H, OAc), 2.02 (s, 3H, OAc), 1.98 (s, 3H, OAc), 1.25 (t, 3H, J=7.0 Hz, C=OCH$_2$CH$_3$).

$^{19}$F-NMR (D$_2$O, 376 MHz)–δ–79.0 (triflate counterion)

Example 1(C): Preparation of Reduced Tribenzoyl Nicotinamide Riboside, Namely tribenzoyl-1,4-dihydronicotinamide riboside, a Compound of Formula (III) (the β-Anomer Form of which is Shown in FIG. 4)

Reduction (unoptimised): A compound of formula (IV), namely tribenzoyl nicotinamide riboside, triflate (—OTf) salt was dissolved in minimal methanol and transferred to a round bottomed flask, 10 mL of H$_2$O was added to the solution and most of the methanol removed via rotary evaporation. The starting material crashed out of solution and 20 mL of diethyl ether (Et$_2$O) was added until the solids solubilized into a biphasic system. A solution of NaHCO$_3$ (420 mg, 5 mmol, 5 eq) and sodium dithionite (348 mg, 2 mmol, 2 eq) in 10 mL H$_2$O was added and stirred for 2 hrs.

The layers were separated and the ether layer was dried over MgSO$_4$ and concentrated to provide 428 mg (76% yield) of tribenzoyl-1,4-dihydronicotinamide riboside (yellow solid) without further purification. 80% purity based on $^1$H-NMR. Pure material is obtained by Biotage purification.

$^1$H-NMR-δ 8.01-8.04 (2H, m, OBz), 7.81-7.86 (4H, m, OBz), 7.25-7.55 (9H, m, OBz), 7.13 (1H, s, H-6), 6.01 (1H, dd, J=8.2, 1.5 Hz, H-7), 5.68 (1H, dd, J=6.2, 3.5 Hz, H-3), 5.57 (1H, dd, J=6.7, 6.2 Hz, H-2), 5.29 (1H, d, J=6.7 Hz, H-1), 4.61-4.68 (2H, m, H-8, H-5), 4.50-4.55 (2H, m, H-4, H-5'), 3.93-3.94 (2H, m, H-9).

$^{13}$C-NMR-δ 172.7, 167.6, 166.7, 166.6 (3× C=O—C$_6$H$_5$, C=ONH$_2$), 138.1 (C-6), 134.9, 134.8, 134.6, 130.9, 130.8, 130.7, 130.3, 130.0, 129.8, 129.7 (3× OBz), 125.7 (C-7), 105.9 (C-8), 94.9 (C-1), 80.3 (C-4), 72.9 (C-2), 72.7 (C-3), 65.4 (C-5), 23.6 (C-9).

The compound of formula (IV), namely tribenzoyl nicotinamide riboside, triflate (—OTf) salt was prepared as follows. Ribose tetraacetate (also known as tetraacetate riboside) was reacted with TMS-nicotinamide (trimethylsilyl N-trimethylsilylpyridine-3-carboximidate, available from Sigma-Aldrich) using the general ball milling Vorbrüggen procedure described in Example 1(A) above. The reactants, namely 1eg 1-acetate-tribenzoate riboside, 1eg TMSOTf and 1eg TMS-nicotinamide, were reacted for 30 mins in a 1.5 ml steel vessel with a 1.5 cm diameter steel ball bearing in a Retsch MM400 mixer mill at 25 Hz. 1eq of DCE (dichloroethylene) was required and the crude reaction mixture (containing some unreacted nicotinamide and starting benzoate sugar, <10%) was used for the reduction step (described above) without further purification. It will be appreciated that the tribenzoyl nicotinamide riboside, triflate (—OTf) salt is not limited to being produced by this exact method, and could, for example, be produced using a conventional Vorbrüggen reaction as described, for example, in International PCT patent publication no. WO 2007/061798 or in T. Yang, N. Y. K. Chan and A. A. Sauve, *Journal of Medicinal Chemistry*, 2007, 50, 6458-6461.

$^1$H-NMR (MeOD, 400 MHz) –δ 9.59 (s, 1H, aromatic), 9.31 (d, 1H, J=6.4 Hz, aromatic), 8.94 (d, 1H, J=8.1 Hz, aromatic), 8.15 (dd, 1H, J=8.1, 6.4 Hz, aromatic), 7.90-7.94 (m, 6H, OBz), 7.50-7.54 (m, 3H, OBz), 7.31-7.38 (m, 6H, OBz), 6.79 (d, 1H, J=3.9 Hz, H-1 (anomeric)), 5.97 (dd, 1H, J=5.6, 3.9 Hz, H-2), 5.87 (t, 1H, J=5.6 Hz, H-3), 5.13-5.16 (m, 1H, H-4), 4.83-4.91 (m, 2H, H-5).

$^{19}$F-NMR (MeOD, 376 MHz)–δ–79.1 (triflate counterion)

Example 2

A compound of formula (II), namely NRH (reduced nicotinamide riboside, also known as 1-(beta-D-ribofuranosyl)-1,4-dihydronicotinamide (the β-anomer form of which is shown in FIG. 4) was prepared as follows. The pH of the reaction medium described in the following example was in the region of about 6-8.

Reduced triacetyl nicotinamide riboside, namely triacetyl-1,4-dihydronicotinamide riboside, a compound of formula (III), prepared in Example 1(A) above, was deprotected using mechanochemical (MeOH, NaOH) processes to remove the acetyl moiety afforded NRH quantitatively. 100 mgs of (III) was dissolved in 0.5 mL of MeOH containing 0.05 g of NaOH. The compounds were reacted for 30 mins in a 1.5 ml steel vessel with a 1.5 cm diameter steel ball bearing in a Retsch MM400 mixer mill at 25 Hz.

$^1$H-NMR (MeOD, 400 MHz) –δ7.18 (s, 1H, H-5), 6.14 (d, 1H, J=8.28 Hz, H-6), 4.85 (m, 1H, H-3), 4.76 (d, 1H, J=5.77 Hz, H-4), 4.04 (m, 2H, H-7&H-8), 3.93 (m, 1H, J=2.76, H-9), 3.72 (ABX, 1H, Jaa=12.55 Hz, Jab=3.51 Hz, H-10), 3.65 (ABX, 1H, Jaa=12.55 Hz, Jab=4.02 Hz, H-10), 3.10 (q, 2H, J=1.51 Hz H-2). 13C-NMR (MeOD, 125 MHz) –δ172.88 (C-11), 137.83 (C-5), 125.29 (C-4), 105.19 (C-6), 95.00 (C-3), 83.54 (C-9), 71.10 (C-8), 70.20 (C-7), 61.61 (C-10), 22.09 (C-2); HRMS m/z: 257.1130; Calc. Mass: 257.1137.

It will be appreciated that the deprotection step as described above may be used to deprotect any other compound of formula (III), including, but not limited to, reduced triacetyl nicotinate ester riboside, namely 2,3,5-triacetyl O-ethyl-1,4-dihydronicotinate riboside, prepared in Example 1(B), and reduced tribenzoyl nicotinamide riboside, namely tribenzoyl-1,4-dihydronicotinamide riboside, prepared in Example 1(C). The deprotection step may also be modified to suit particular requirements.

Example 3

Compounds of formula (I) were prepared in accordance with the invention as follows. The pH of the reaction media described in the following examples was in the region of about 6-8.

Example 3(A): Preparation of Nicotinamide Riboside, Chloride Salt (the β-Anomer Form of which is Shown in FIG. 5)

A compound of formula (II), namely NRH (reduced nicotinamide riboside, shown in FIG. 2; 50 mg, 0.20 mmol, 1 eq), was dissolved in 5 mL H$_2$O and then 1 eq (i.e. 0.20 mmol) of ammonium chloride was added in one portion. Activated charcoal (~10 mg, i.e. 0.80 mmol) was then added and the mixture stirred at RT for ~1 hr and then filtered and freeze-dried to give the chloride salt of nicotinamide riboside, quantitatively, i.e. 100% conversion and pure product.

$^1$H-NMR (D$_2$O, 400 MHz) –δ 9.46 (s, 1H, aromatic), 9.12 (dt, 1H, J=6.3, 1.4 Hz, aromatic), 8.83 (dt, 1H, J=8.2, 1.4 Hz, aromatic), 8.13 (dd, 1H, J=8.2, 6.3 Hz, aromatic), 6.13 (d, 1H, J=4.3 Hz, H-1 (anomeric)), 4.37 (t, 1H, J=4.7 Hz, H-2), 4.31-4.34 (m, 1H, H-4), 4.21 (t, 1H, J=4.7 Hz, H-3), 3.90 (ABX, 1H, J$_{a,a'}$=13.0 Hz, J$_{a,b}$=3.5 Hz, H-5), 3.75 (ABX, 1H, J$_{a,a'}$=13.0 Hz, J$_{a',b}$=2.8 Hz, H-5').

It will be appreciated that the NRH may be that obtained in Example 2, or may be obtained commercially from e.g. Diverchim, 100, rue Louis Blanc, 60 765 Montataire Cedex, France—(CAS Registry Number:19132-12-8) either as a pure product or as a mixture of anomers.

Example 3(B): Preparation of Nicotinamide Riboside, Acetate Salt (the β-Anomer Form of which is Shown in FIG. 5)

The method described in Example 3(A) was carried out, except that 1 eq (i.e. 0.20 mmol) of ammonium acetate was added. The acetate salt of nicotinamide riboside was obtained, quantitatively.

$^1$H-NMR (D$_2$O, 400 MHz) –δ 9.46 (s, 1H, aromatic), 9.12 (d, 1H, J=6.3 Hz, aromatic), 8.83 (d, 1H, J=8.2 Hz, aromatic), 8.12 (m, 1H, aromatic), 6.09 (d, 1H, J=4.4 Hz, H-1 (anomeric)), 4.36 (t, 1H, J=4.7 Hz, H-2), 4.32-4.35 (m, 1H, H-4), 4.21 (t, 1H, J=4.7 Hz, H-3), 3.91 (ABX, 1H, J$_{a,a'}$=13.1 Hz, J$_{a,b}$=2.8 Hz, H-5), 3.75 (ABX, 1H, J$_{a,a'}$=13.0 Hz, J$_{a',b}$=3.5 Hz, H-5'), 1.79 (s, 3H, OAC).

Example 3(C): Preparation of Nicotinamide Riboside, Formate Salt (the β-Anomer Form of which is Shown in FIG. 5)

The method described in Example 3(A) was carried out, except that 1 eq (i.e. 0.20 mmol) of ammonium formate (methanoate) was added. The formate salt of nicotinamide riboside was obtained, quantitatively.

$^1$H-NMR (D$_2$O, 400 MHz) –δ 9.46 (s, 1H, aromatic), 9.12 (d, 1H, J=6.3 Hz, aromatic), 8.83 (d, 1H, J=8.2 Hz, aromatic), 8.29 (s, 1H, formate), 8.12 (m, 1H, aromatic), 6.09 (d, 1H, J=4.4 Hz, H-1 (anomeric)), 4.36 (t, 1H, J=4.7 Hz, H-2), 4.31-4.34 (m, 1H, H-4), 4.21 (t, 1H, J=4.7 Hz, H-3), 3.91 (ABX, 1H, $J_{a,a'}$=13.1 Hz, $J_{a,b}$=3.5 Hz, H-5), 3.79 (ABX, 1H, $J_{a,a'}$=13.0 Hz, $J_{a',b}$=2.8 Hz, H-5').

Example 3(D): Preparation of Nicotinamide Riboside, Trifluoroacetate Salt (the β-Anomer Form of which is Shown in FIG. 5)

The method described in Example 3(A) was carried out, except that leg (i.e. 0.20 mmol) of ammonium trifluoroacetate was added. The trifluoroacetate salt of nicontinamide riboside was obtained, quantitatively.

$^1$H-NMR (D$_2$O, 400 MHz) –δ 9.46 (s, 1H, aromatic), 9.12 (d, 1H, J=6.3 Hz, aromatic), 8.83 (d, 1H, J=8.2, aromatic), 8.13 (dd, 1H, J=8.2, 6.3 Hz, aromatic), 6.13 (d, 1H, J=4.3 Hz, H-1 (anomeric)), 4.35 (t, 1H, J=4.7 Hz, H-2), 4.31-4.34 (m, 1H, H-4), 4.20 (t, 1H, J=4.7 Hz, H-3), 3.89 (ABX, 1H, $J_{a,a'}$=13.0 Hz, $J_{a,b}$=3.6 Hz, H-5), 3.74 (ABX, 1H, $J_{a,a'}$=13.0 Hz, $J_{a',b}$=2.9 Hz, H-5'). $^{19}$F-NMR (D$_2$O, 376 MHz)–δ–75.7 (CF$_3$COO$^-$).

Example 3(E): Preparation of Nicotinamide Riboside, Chloride Salt (the β-Anomer Form of which is Shown in FIG. 5)

An alternative method to that described in Example 3(A) was carried out as follows. NRH (reduced nicotinamide riboside, shown in FIG. 4; 50 mg, 0.20 mmol, leg) was dissolved in 5 mL H$_2$O:EtOAc (1:1) and then leg. (i.e. 0.20 mmol) of ammonium chloride was added in one portion. Upon work-up after 1 hr, no oxidation had taken place and the starting materials were fully recovered. The recovered NRH and ammonium chloride were re-suspended in the same solvent system with addition of activated charcoal (~10 mg, i.e. 0.8 mmol) and stirred at RT for 1 hr. Subsequent filtration and freeze-drying afforded the chloride salt of nicotinamide riboside in quantitative yield. Thus it was concluded that a carbon-containing catalyst, e.g. activated charcoal, was essential to the method.

$^1$H-NMR (D$_2$O, 400 MHz) –δ 9.46 (s, 1H, aromatic), 9.12 (dt, 1H, J=6.3, 1.4 Hz, aromatic), 8.83 (dt, 1H, J=8.2, 1.4 Hz, aromatic), 8.13 (dd, 1H, J=8.2, 6.3 Hz, aromatic), 6.13 (d, 1H, J=4.3 Hz, H-1 (anomeric)), 4.37 (t, 1H, J=4.7 Hz, H-2), 4.31-4.34 (m, 1H, H-4), 4.21 (t, 1H, J=4.7 Hz, H-3), 3.90 (ABX, 1H, $J_{a,a'}$=13.0 Hz, $J_{a,b}$=3.5 Hz, H-5), 3.75 (ABX, 1H, $J_{a,a'}$=13.0 Hz, $J_{a',b}$=2.8 Hz, H-5').

Example 3(F): Preparation of Nicotinamide Riboside, Chloride Salt (the β-Anomer Form of which is Shown in FIG. 5)

The method described in Example 3(E) was carried out, except that NRH (reduced nicotinamide riboside, shown in FIG. 4; 50 mg, 0.20 mmol, 1 eq) was dissolved in 5 mL H$_2$O:THF (1:1), instead of H$_2$O:EtOAc (1:1), and then 1 eq (i.e. 0.20 mmol) of ammonium chloride was added in one portion. Upon work-up after 1 hr, no oxidation had taken place and the starting materials were fully recovered. The recovered NRH and ammonium chloride were re-suspended in the same solvent system with addition of activated charcoal (~10 mg, i.e. 0.8 mmol) and stirred at RT for 1 hr. Subsequent filtration and freeze-drying afforded the chloride salt of nicotinamide riboside in quantitative yield. Thus it was concluded that a carbon-containing catalyst, e.g. activated charcoal, was essential to the method.

$^1$H-NMR (D$_2$O, 400 MHz) –δ 9.46 (s, 1H, aromatic), 9.12 (dt, 1H, J=6.3, 1.4 Hz, aromatic), 8.83 (dt, 1H, J=8.2, 1.4 Hz, aromatic), 8.13 (dd, 1H, J=8.2, 6.3 Hz, aromatic), 6.13 (d, 1H, J=4.3 Hz, H-1 (anomeric)), 4.37 (t, 1H, J=4.7 Hz, H-2), 4.31-4.34 (m, 1H, H-4), 4.21 (t, 1H, J=4.7 Hz, H-3), 3.90 (ABX, 1H, $J_{a,a'}$=13.0 Hz, $J_{a,b}$=3.5 Hz, H-5), 3.75 (ABX, 1H, $J_{a,a'}$=13.0 Hz, $J_{a',b}$=2.8 Hz, H-5').

The invention claimed is:

1. A compound of formula (IV):

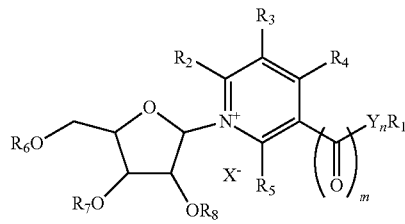

or the beta-anomer thereof, where:

n is 0 and Y is absent;

m is 1;

R$_1$ is a substituted or unsubstituted primary amino;

R$_2$-R$_5$ are each H;

R$_6$, R$_7$ and R$_8$, which may be the same or different, are each independently H or a hydroxyl-protecting group; or wherein R$_6$ is a phosphate; and X$^-$ is an anion selected from an anion of a substituted carboxylic acid, an anion of an unsubstituted carboxylic acid other than an anion of formic acid, an anion of a substituted or unsubstituted phosphate, an anion of a substituted or unsubstituted sulfate, an anion of a substituted or unsubstituted carbonate, and an anion of a substituted or unsubstituted carbamate.

2. The compound of claim 1, wherein R$_1$ is —NH$_2$.

3. The compound of claim 1, wherein R$_6$, R$_7$ and R$_8$, which may be the same or different, are each independently H or a hydroxyl-protecting group.

4. The compound of claim 3, wherein X$^-$ is an anion, selected from an anion of an unsubstituted carboxylic acid other than an anion of formic acid, an anion of an unsubstituted phosphate, an anion of an unsubstituted sulfate, an anion of an unsubstituted carbonate, and an anion of an unsubstituted carbamate.

5. The compound of claim 3, wherein X$^-$ is an anion of a substituted monocarboxylic acid or an anion of an unsubstituted monocarboxylic acid other than an anion of formic acid.

6. A compound of formula (IV):

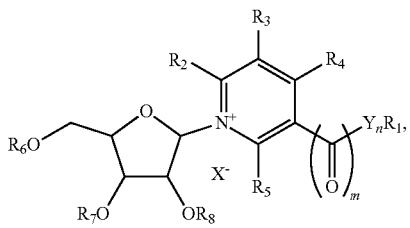

or the beta-anomer thereof,
where:
n is 0 and Y is absent;
m is 1;
$R_1$ is a substituted or unsubstituted primary amino;
$R_2$-$R_5$ are each H;
$R_6$, $R_7$ and $R_8$, which may be the same or different, are each independently H or a hydroxyl-protecting group; or where $R_6$ is a phosphate; and
$X^-$ is an anion of a substituted or unsubstituted aminodicarboxylic acid.

7. The compound of claim 1, wherein $X^-$ is selected from the group consisting of acetate, trifluoroacetate, ascorbate, lactate, propionate and butyrate.

8. The compound of claim 1 of formula:

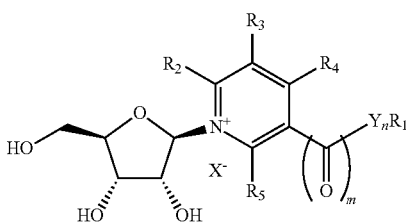

where:
n is 0 and Y is absent;
m is 1;
$R_1$ is —$NH_2$
$R_2$-$R_5$ are each H; and
$X^-$ is an anion of a substituted monocarboxylic acid or an anion of an unsubstituted monocarboxylic acid other than formic acid.

9. The compound according to claim 1 of formula:

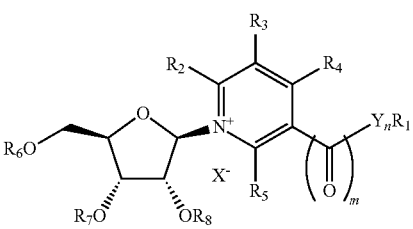

where:
n is 0 and Y is absent;
m is 1;
$R_1$ is —$NH_2$
$R_2$-$R_5$ are each H;

$R_6$, $R_7$ and $R_8$, which may be the same or different, are each independently a hydroxyl-protecting group selected from unsubstituted acetyl, and unsubstituted benzoyl; and
$X^-$ is an anion of a substituted monocarboxylic acid, or an anion of an unsubstituted monocarboxylic acid other than formic acid.

10. A nutritional supplement composition comprising a compound of claim 1.

11. The nutritional supplement composition of claim 10, wherein $R_1$ is —$NH_2$ and $X^-$ is an anion of a substituted or unsubstituted dicarboxylic acid.

12. The nutritional supplement composition of claim 10, wherein $R_1$ is —$NH_2$ and $R_6$, $R_7$ and $R_8$, which may be the same or different, are each independently H or a hydroxyl-protecting group selected from unsubstituted acetyl, and unsubstituted benzoyl.

13. A method of making an isomerically pure compound of formula (IV) having a beta-D-ribofuranosyl configuration:

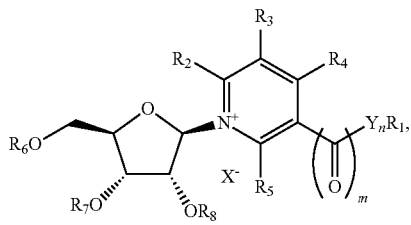

the method comprising the step of:
introducing the anion $X^-$ into a starting isomerically pure trifluoromethanesulfonate compound of formula having a beta-D-ribofuranosyl configuration:

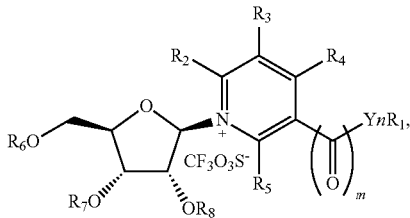

by reacting the starting trifluoromethanesulfonate compound, with a compound of formula $Z^+X^-$,
where:
n is 0 or 1;
m is 0 or 1;
Y═O or S:
$R_1$ is selected from H, substituted or unsubstituted alkyl, substituted or unsubstituted alkenyl, substituted or unsubstituted alkynyl, substituted or unsubstituted aryl, substituted or unsubstituted primary or secondary amino, and unsubstituted azido;
$R_2$-$R_5$, which may be the same or different, are each independently selected from H, substituted or unsubstituted alkyl, substituted or unsubstituted alkenyl, substituted or unsubstituted alkynyl, and substituted or unsubstituted aryl;
$R_6$-$R_8$, which may be the same or different, are each independently H or a hydroxyl-protecting group; or wherein $R_6$ is a phosphate;

X⁻ is an anion selected from an anion of a substituted or unsubstituted carboxylic acid, a halide, a substituted or unsubstituted sulfonate other than trifluoromethanesulfonate, a substituted or unsubstituted phosphate, a substituted or unsubstituted sulfate, a substituted or unsubstituted carbonate, and a substituted or unsubstituted carbamate, and Z⁺ is a nitrogen-containing cation.

14. The method of claim 13, wherein $R_1$ is —$NH_2$.

15. The method of claim 13, wherein $R_6$, $R_7$ and $R_8$, which may be the same or different, are each independently H or a hydroxyl-protecting group selected from unsubstituted acetyl, and unsubstituted benzoyl.

16. The method of claim 13, where the nitrogen containing cation is selected from a substituted or unsubstituted ammonium, a substituted or unsubstituted pyridinium, a substituted or unsubstituted pyrrolidinium, a substituted or unsubstituted imidazolium and a substituted or unsubstituted triazolium.

17. The method of claim 13, where Z⁺ is a substituted or unsubstituted ammonium of the formula $N^+HR'R''R'''$, wherein $R'$, $R''$ and $R'''$, which may be the same or different, are each independently selected from H, substituted or unsubstituted alkyl, substituted or unsubstituted alkenyl, substituted or unsubstituted alkynyl, and substituted or unsubstituted aryl.

18. A method of making an isomerically pure compound of formula (IV) having a beta-D-ribofuranosyl configuration:

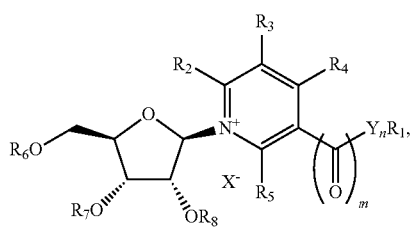

the method comprising the step of:
introducing the anion X-into a starting isomerically pure trifluoromethanesulfonate compound of formula having a beta-D-ribofuranosyl configuration:

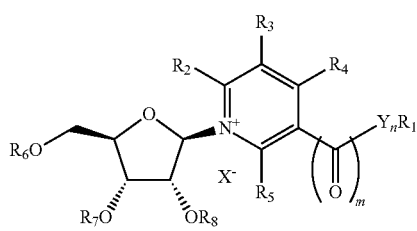

by reacting the starting trifluoromethanesulfonate compound, with a compound of formula $Z^+X^-$,
where:
n is 0 and Y is absent;
m is 1;
$R_1$=$NH_2$;
$R_2$-$R_5$ are each H;
$R_6$, $R_7$ and $R_8$, which may be the same or different, are each independently H or a hydroxyl-protecting group; or wherein $R_6$ is a phosphate;

X⁻ is an anion, selected from an anion of a substituted or unsubstituted carboxylic acid, a halide, a substituted or unsubstituted phosphate, a substituted or unsubstituted sulfate, a substituted or unsubstituted carbonate, and a substituted or unsubstituted carbamate; and Z⁺ is a nitrogen-containing cation.

19. The method of claim 18, wherein $R_6$, $R_7$ and $R_8$, which may be the same or different, are each independently H or a hydroxyl-protecting group selected from unsubstituted acetyl, and unsubstituted benzoyl; and X⁻ is an anion, selected from an anion of a substituted or unsubstituted carboxylic acid and a halide.

20. The method of claim 18, wherein X⁻ is an anion of a substituted or unsubstituted monocarboxylic acid.

21. The compound of claim 1, wherein $R_6$, $R_7$ and $R_8$, which may be the same or different, are each independently H or a hydroxyl-protecting group selected from unsubstituted acetyl, and unsubstituted benzoyl.

22. The compound of claim 2, wherein X⁻ is an anion of a substituted or unsubstituted dicarboxylic acid.

23. The compound of claim 6, wherein X⁻ is selected from aspartate and glutamate.

24. The compound of claim 6, wherein the compound is the beta-anomer;
n is 0 and Y is absent;
m is 1;
$R_1$ is —$NH_2$;
$R_2$-$R_5$ are each H;
$R_6$, $R_7$ and $R_8$ are each H; and
X⁻ is an anion of a substituted or unsubstituted aminodicarboxylic acid.

25. The compound of claim 6, wherein the compound is the beta-anomer;
n is 0 and Y is absent;
m is 1;
$R_1$ is —$NH_2$;
$R_2$-$R_5$ are each H;
$R_6$, $R_7$ and $R_8$, which may be the same or different, are each independently a hydroxyl-protecting group selected from unsubstituted acetyl, and unsubstituted benzoyl; and
X⁻ is an anion of a substituted or unsubstituted aminodicarboxylic acid.

26. The compound of claim 1 of formula:

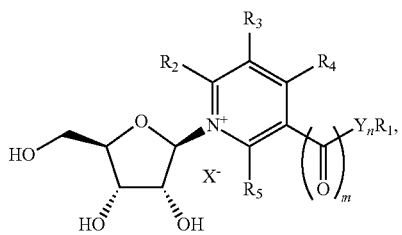

where:
n is 0 and Y is absent;
m is 1;
$R_1$ is —$NH_2$;
$R_2$-$R_5$ are each H; and
X⁻ is an anion of a substituted or unsubstituted dicarboxylic acid.

27. The compound of claim 1 of formula:

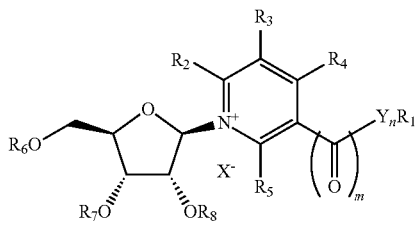

where:
n is 0 and Y is absent;
m is 1;
$R_1$ is —$NH_2$;
$R_2$-$R_5$ are each H;
$R_6$, $R_7$ and $R_8$, which may be the same or different, are each independently a hydroxyl-protecting group selected from unsubstituted acetyl, and unsubstituted benzoyl; and
$X^-$ is an anion of a substituted or unsubstituted dicarboxylic acid.

28. The compound of claim 1 that is a beta-anomer.

29. The compound of claim 1 that is a beta-anomer; wherein the compound has greater than 90% chemical purity, and comprises at least 98% diastereomeric purity of the beta-D-ribofuranosyl configuration.

30. The compound of claim 1 that is a beta-anomer; wherein the compound has greater than 90% chemical purity, comprises at least 98% diastereomeric purity of the beta-D-ribofuranosyl configuration; and contains <3000 ppm methanol, under 0.1% (w/w) other solvents and under 0.2% (w/w) water.

31. The compound of claim 6 that is a beta-anomer.

32. The compound of claim 6 that is a beta-anomer; wherein the compound has greater than 90% chemical purity, and comprises at least 98% diastereomeric purity of the beta-D-ribofuranosyl configuration.

33. The compound of claim 6 that is a beta-anomer; wherein the compound has greater than 90% chemical purity, comprises at least 98% diastereomeric purity of the beta-D-ribofuranosyl configuration; and contains <3000 ppm methanol, under 0.1% (w/w) other solvents and under 0.2% (w/w) water.

34. A nutritional supplement composition comprising a compound of claim 6.

35. The nutritional supplement composition of claim 34, wherein $R_1$ is —$NH_2$.

36. The method of claim 18, wherein $X^-$ is an anion of a substituted or unsubstituted dicarboxylic acid.

37. A method of making an isomerically pure compound of formula (IV) having a beta-D-ribofuranosyl configuration:

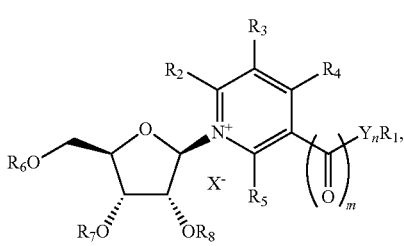

the method comprising the step of:
introducing the anion $X^-$ into a starting isomerically pure trifluoromethanesulfonate compound of formula having a beta-D-ribofuranosyl configuration:

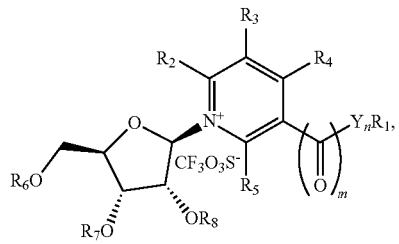

by reacting the starting trifluoromethanesulfonate compound, with a compound of formula $Z^+X^-$, wherein:
n is 0 or 1;
m is 0 or 1;
Y=O or S;
$R_1$ is selected from H, substituted or unsubstituted alkyl, substituted or unsubstituted alkenyl, substituted or unsubstituted alkynyl, substituted or unsubstituted aryl, substituted or unsubstituted primary or secondary amino, and unsubstituted azido;
$R_2$-$R_5$, which may be the same or different, are each independently selected from H, substituted or unsubstituted alkyl, substituted or unsubstituted alkenyl, substituted or unsubstituted alkynyl, and substituted or unsubstituted aryl;
$R_6$-$R_8$, which may be the same or different, are each independently H or a hydroxyl-protecting group;
$X^-$ is an anion of a substituted or unsubstituted aminodicarboxylic acid; and
$Z^+$ is a nitrogen-containing cation.

38. The method of claim 13, wherein the compound is a beta-anomer; and wherein the compound has greater than 90% chemical purity, and comprises at least 98% diastereomeric purity of the beta-D-ribofuranosyl configuration.

39. The method of claim 13, wherein the compound is a beta-anomer; and wherein the compound has greater than 90% chemical purity, comprises at least 98% diastereomeric purity of the beta-D-ribofuranosyl configuration; and contains <3000 ppm methanol, under 0.1% (w/w) other solvents and under 0.2% (w/w) water.

40. The method of claim 18, wherein the compound is a beta-anomer; and wherein the compound has greater than 90% chemical purity, and comprises at least 98% diastereomeric purity of the beta-D-ribofuranosyl configuration.

41. The method of claim 18, wherein the compound is a beta-anomer; and wherein the compound has greater than 90% chemical purity, comprises at least 98% diastereomeric purity of the beta-D-ribofuranosyl configuration; and contains <3000 ppm methanol, under 0.1% (w/w) other solvents and under 0.2% (w/w) water.

42. The method of claim 37, wherein the compound is a beta-anomer; and wherein the compound has greater than 90% chemical purity, and comprises at least 98% diastereomeric purity of the beta-D-ribofuranosyl configuration.

43. The method of claim 37, wherein the compound is a beta-anomer; and wherein the compound has greater than 90% chemical purity, comprises at least 98% diastereomeric purity of the beta-D-ribofuranosyl configuration; and contains <3000 ppm methanol, under 0.1% (w/w) other solvents and under 0.2% (w/w) water.

* * * * *

UNITED STATES PATENT AND TRADEMARK OFFICE
CERTIFICATE OF CORRECTION

PATENT NO. : 12,252,506 B2  
APPLICATION NO. : 18/307733  
DATED : March 18, 2025  
INVENTOR(S) : Marie Migaud et al.

Page 1 of 1

It is certified that error appears in the above-identified patent and that said Letters Patent is hereby corrected as shown below:

In the Claims

In Column 20, Claim 13, Line 54, please replace "Y==O or S;" with --Y = O or S;--.

In Column 21, Claim 18, Line 43, please replace "X-into" with --X⁻ into--.

In Column 21, Claim 18, Line 63, please replace "$R_1$==$NH_2$" with --$R_1$ = $NH_2$--.

In Column 24, Claim 37, Line 21, please replace "Y==O or S;" with --Y = O or S;--.

Signed and Sealed this  
Eleventh Day of November, 2025

John A. Squires  
*Director of the United States Patent and Trademark Office*